(12) United States Patent
Hamilton et al.

(10) Patent No.: US 12,147,761 B2
(45) Date of Patent: Nov. 19, 2024

(54) SYSTEMS AND METHODS FOR IMPROVED SPELL CHECK

(71) Applicant: Optum, Inc., Minnetonka, MN (US)

(72) Inventors: Laura D. Hamilton, Chicago, IL (US); Vinit Garg, Fremont, CA (US); Ayush Tomar, Morgan Hill, CA (US); Fazle Shahnawaz Muhibul Karim, Chicago, IL (US); Chenwei Liu, Rockville, MD (US)

(73) Assignee: Optum, Inc., Minnetonka, MN (US)

( * ) Notice: Subject to any disclaimer, the term of this patent is extended or adjusted under 35 U.S.C. 154(b) by 0 days.

(21) Appl. No.: 18/355,488

(22) Filed: Jul. 20, 2023

(65) Prior Publication Data

US 2024/0281604 A1   Aug. 22, 2024

Related U.S. Application Data

(60) Provisional application No. 63/485,729, filed on Feb. 17, 2023.

(51) Int. Cl.
| | |
|---|---|
| *G06F 17/00* | (2019.01) |
| *G06F 16/215* | (2019.01) |
| *G06F 16/9032* | (2019.01) |
| *G06F 16/9038* | (2019.01) |
| *G06F 40/232* | (2020.01) |

(Continued)

(52) U.S. Cl.
CPC .......... *G06F 40/232* (2020.01); *G06F 16/215* (2019.01); *G06F 16/90328* (2019.01); *G06F 16/9038* (2019.01); *G06F 40/242* (2020.01); *G16H 10/60* (2018.01)

(58) Field of Classification Search
CPC .... G06F 40/232; G06F 40/242; G06F 16/215; G06F 16/90328; G06F 16/9038; G16H 10/60
See application file for complete search history.

(56) References Cited

U.S. PATENT DOCUMENTS

| | | | |
|---|---|---|---|
| 6,292,771 B1 | 9/2001 | Haug et al. | |
| 7,254,774 B2 * | 8/2007 | Cucerzan ............ | G06F 16/9532 715/257 |

(Continued)

FOREIGN PATENT DOCUMENTS

| | | | |
|---|---|---|---|
| CN | 101131706 B | * | 10/2010 |
| CN | 113190739 A | * | 7/2021 |

*Primary Examiner* — Laurie A Ries
(74) *Attorney, Agent, or Firm* — Bookoff McAndrews, PLLC

(57) ABSTRACT

Systems and methods for improved spelling checking are disclosed. A method includes receiving a search query from a user device and determining that the search query does not exist in a data store that stores (a) a corpus of correctly spelled words or (b) forced correction mapping data. The method further includes, in response to the determining, determining a plurality of suggested search queries generated by a plurality of respective spell corrector models, selecting a suggested search query determined using a spell corrector model from the plurality of spell corrector models based on at least one of a frequency of the suggested search query in historical search data or a weightage associated with the spell corrector model, and causing the suggested search query to be displayed on the user device.

20 Claims, 7 Drawing Sheets

(51) Int. Cl.
*G06F 40/242* (2020.01)
*G16H 10/60* (2018.01)

(56) References Cited

U.S. PATENT DOCUMENTS

| | | | | |
|---|---|---|---|---|
| 8,583,670 | B2* | 11/2013 | Cameron | G06F 16/3322 |
| | | | | 707/765 |
| 9,275,106 | B2* | 3/2016 | Djabarov | G06F 16/3325 |
| 9,317,606 | B1* | 4/2016 | Nayak | G06F 16/951 |
| 11,151,317 | B1* | 10/2021 | Singh | G06F 40/232 |
| 2005/0210383 | A1* | 9/2005 | Cucerzan | G06F 40/232 |
| | | | | 715/257 |
| 2007/0088695 | A1* | 4/2007 | Bleyendaal | G16H 10/60 |
| | | | | 707/999.005 |
| 2008/0046405 | A1* | 2/2008 | Olds | G06F 16/3322 |
| 2011/0295897 | A1* | 12/2011 | Gao | G06F 16/3322 |
| | | | | 707/780 |
| 2012/0284308 | A1* | 11/2012 | Paduroiu | G06F 40/232 |
| | | | | 707/E17.014 |
| 2013/0060560 | A1* | 3/2013 | Mahkovec | G06F 40/232 |
| | | | | 704/9 |
| 2013/0124492 | A1* | 5/2013 | Gao | G06F 40/232 |
| | | | | 707/706 |
| 2013/0346400 | A1* | 12/2013 | Ramsey | G06F 16/951 |
| | | | | 707/E17.084 |
| 2013/0346434 | A1* | 12/2013 | Shazeer | G06F 40/232 |
| | | | | 707/759 |
| 2015/0095185 | A1* | 4/2015 | Katukuri | G06F 16/9535 |
| | | | | 707/723 |
| 2016/0042001 | A1* | 2/2016 | Lightner | G06F 16/90328 |
| | | | | 707/728 |
| 2016/0179961 | A1* | 6/2016 | Wu | G06F 16/3322 |
| | | | | 707/706 |
| 2019/0108235 | A1* | 4/2019 | Zheng | G06F 16/24578 |
| 2019/0236132 | A1* | 8/2019 | Zhu | G06N 20/00 |
| 2019/0370393 | A1* | 12/2019 | Finch | G06F 16/3338 |
| 2020/0019632 | A1* | 1/2020 | Larchev | G06F 16/242 |
| 2020/0242148 | A1 | 7/2020 | Mankovich et al. | |
| 2021/0090694 | A1* | 3/2021 | Colley | G16H 15/00 |
| 2022/0067074 | A1 | 3/2022 | O'Neil et al. | |
| 2022/0382818 | A1* | 12/2022 | Chen | H04L 67/535 |

* cited by examiner

SYSTEMS AND METHODS FOR IMPROVED SPELL CHECK

CROSS-REFERENCE TO RELATED APPLICATION(S)

The present application claim priority to U.S. Provisional Patent Application No. 63/485,729, titled "SYSTEMS AND METHODS FOR IMPROVED SPELL CHECK," filed Feb. 17, 2023, the entire disclosure of which is hereby incorporated by reference.

TECHNICAL FIELD

The present disclosure relates generally to spell checking. More particularly, the present disclosure relates to systems and methods for determining a plurality of suggested search queries, each search query being determined by a spell corrector from a plurality of spell corrector models and selecting a suggested search query from the plurality of suggested search queries.

BACKGROUND

Users search various queries in mobile and web applications. However, these queries may contain misspellings, which can yield unwanted search results. For example, 1 in 10 queries are misspelled in Google. Misspellings in the healthcare domain may frequently occur as healthcare queries can be very specialized. A spelling corrector may correct these misspellings, save a user time correcting these spellings, and improve search results.

Existing spell checkers (e.g., spelling correctors) generally are not personalized. For example, most existing spell checkers do not integrate patient claims information nor do they integrate prior search information (e.g., search history) of a single user. Typically, when an ensemble (e.g., group) of spell checker models is used, the ensemble works based on an order or a priority of the models. For example, an ensemble of models A, B, and C, may operate as follows: first model A, then model B, and then model C. However, the order of the models within an ensemble may not correspond to the best or optimal model for spelling correction.

The techniques of this disclosure may solve one or more of the problems set forth above and/or other problems in the art. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY OF THE DISCLOSURE

The techniques of the present disclosure solve the problem(s) discussed above and other problems described elsewhere in the present disclosure and improve the state of search optimization and spell checking/correction by providing a spell corrector model that integrates data for a user and is based on multiple spell corrector models to select a suggested spelling correction for a search query that is the most accurate for the user.

In some aspects, the techniques described herein relate to a computer-implemented method for improved spell checking. The method includes receiving, by one or more processors, a search query from a user device; determining, by the one or more processors, that the search query does not exist in a data store that stores (a) a corpus of correctly spelled words or (b) forced correction mapping data; in response to the determining: determining, by the one or more processors, a plurality of suggested search queries generated by a plurality of respective spell corrector models, selecting, by the one or more processors, a suggested search query determined using a spell corrector model from the plurality of spell corrector models based on at least one of a frequency of the suggested search query in historical search data or a weightage associated with the spell corrector model, and causing, by the one or more processors, the suggested search query to be displayed on the user device.

In other aspects, the techniques described herein relate to a system for improved spell checking. The system includes a memory having processor-readable instructions stored therein; and one or more processors configured to access the memory and execute the processor-readable instructions to perform operations comprising: receiving a search query from a user device; determining that the search query does not exist in a data store that stores (a) a corpus of correctly spelled words or (b) forced correction mapping data; in response to the determining: determining a plurality of suggested search queries generated by a plurality of respective spell corrector models, selecting a suggested search query determined using a spell corrector model from the plurality of spell corrector models based on at least one of a frequency of the suggested search query in historical search data or a weightage associated with the spell corrector model, and causing the suggested search query to be displayed on the user device.

In further aspects, the techniques described herein relate to a non-transitory computer readable medium for improved spell checking. The non-transitory computer-readable medium stores a set of instructions for improved spell checking that, when executed by one or more processors, cause the one or more processors to: receive a search query from a user device; determine that the search query does not exist in a data store that stores (a) a corpus of correctly spelled words or (b) forced correction mapping data; in response to the determining: determine a plurality of suggested search queries generated by a plurality of respective spell corrector models, select a suggested search query determined using a spell corrector model from the plurality of spell corrector models based on at least one of a frequency of the suggested search query in historical search data or a weightage associated with the spell corrector model, and cause to display the suggested search query on the user device.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate various example embodiments and together with the description, serve to explain the principles of the disclosed embodiments.

DETAILED DESCRIPTION

Figure 1:
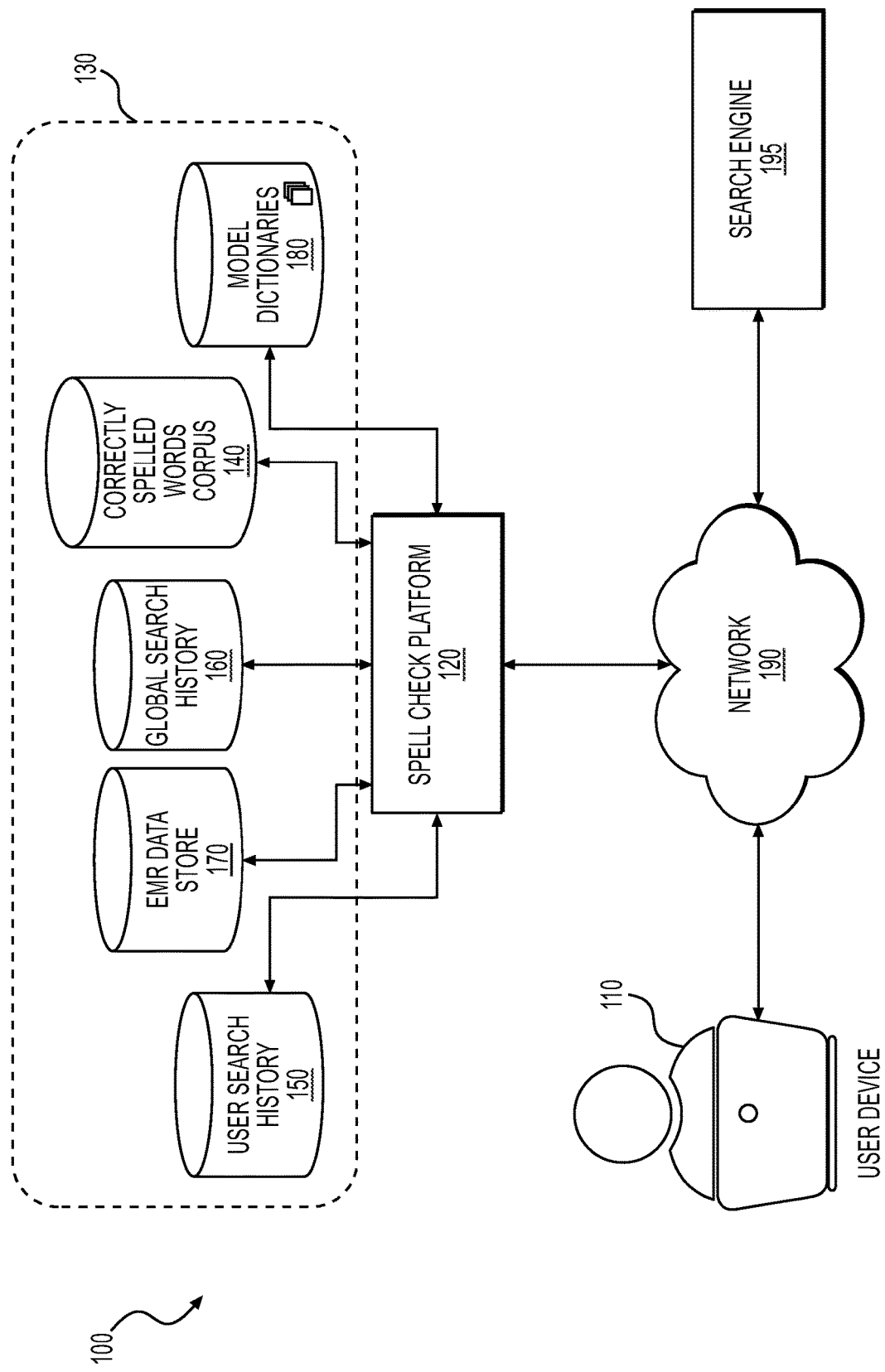
FIG. 1 depicts a block diagram of an example system for spell checking a search query, according to one or more embodiments.

Various embodiments of the present disclosure relate generally to spell checking. More particularly, various embodiments of the present disclosure relate to systems, computer-implemented methods, and non-transitory computer readable media for determining a plurality of suggested search queries, each search query being determined by a spell corrector from a plurality of spell corrector models and selecting a suggested search query from the plurality of suggested search queries.

As discussed above, misspelled search queries occur frequently in the healthcare industry. However, existing spell checkers do not integrate patient claims information nor do they integrate prior search history of a single user. Existing spell checkers may also fail to consider unique queries. For example, when a user searches the misspelled search query "acetahoxamide", an existing spell corrector may recommend "acetazolamide" and "acetohexamide" as query corrections. However, this provides no indication of which query the user should proceed with. Acetohexamide is a first generation sulfonyurea medication used to treat type 2 diabetes, while acetazolamide is a diuretic used to treat glaucoma. Although both of these queries are correctly spelled, they will return vastly different search results. Even to the extent that an ensemble of multiple spell correction models are used, existing ensemble models work based on an order or a priority of the models. However, ensemble models solely based on an order of the models may not suggest the best spelling correction for a particular user. Another deficiency of existing spell corrector models is that they may correct the spelling of a query, but not the grammar.

Conventional spell corrector models often provide inaccurate spelling corrections for misspelled medical related search queries, which typically results in inefficient and time-consuming searching as well as the generation of search results that are not relevant to a patient. Such conventional models routinely use generic dictionaries, search history associated with a wide variety of users, and/or are trained using non-medical related data in order to generate a suggested spelling correction. As such, the conventional techniques fail to account for highly specialized and highly personalized nature of search queries, such as in the healthcare domain. Further, conventional techniques for spell checking and correction generally rely on a single model and a single dictionary. Even when multiple spell corrector models are used together in an ensemble (e.g., in applications other than spell checking), traditional ensemble models do not return a suggested search query that is customized to an individual user. Nor do they return a suggested search query that not only is correctly spelled, but that also is the most accurate for complex queries.

Embodiments of the present disclosure provide a technical improvement to the technical problems that arise in spell-checking applications as discussed above, by providing a spell corrector model that integrates data for a user and is based on multiple spell corrector models to select a suggested spelling correction for a search query that is the most accurate for the user. Compared to the conventional techniques discussed above, the techniques of the present disclosure utilize user data as well as selection logic for selecting the most relevant suggestion from a plurality of suggestions generated by an ensemble model, and thus increases accuracy and efficiency in the context of spell checking and searching. In some embodiments, the selection logic may be based on frequency of a suggestion or a weightage associated with any one or more of the multiple spell corrector models included in the ensemble model.

Motivated from the limitations of existing spell check systems and ensemble spell correction models, techniques herein utilize historical data, such as personal historical data, for optimal spell correction. In one embodiment, the historical data includes medical data and pharmaceutical data as well as the prior search history data (including frequency of search terms) associated with the user who input a misspelled search query. The historical data may further include global search historical data for all users on a platform, wherein the correctly spelled search terms are stored with their corresponding frequencies. Aspects disclosed herein provide personalized spell checking and correction in a medical context. Techniques herein also utilize a plurality of spell corrector models each using a different dictionary to provide various options for search query spell correction and a model selector to select the optimal spell correction candidate. Aspects disclosed herein also provide a method of determining the optimal search query suggestion from a plurality of suggested search queries each being generated by a spell corrector model from a plurality of spell corrector models, where the frequency of the suggested search query is a determining factor.

The terminology used herein may be interpreted in its broadest reasonable manner, even though it is being used in conjunction with a detailed description of certain specific examples of the present disclosure. Indeed, certain terms may even be emphasized below; however, any terminology intended to be interpreted in any restricted manner will be overtly and specifically defined as such in this Detailed Description section. Both the foregoing general description and the following detailed description are exemplary and explanatory only and are not restrictive of the features, as claimed.

In the detailed description herein, references to "embodiment," "an embodiment," "one non-limiting embodiment," "in various embodiments," etc., indicate that the embodiment(s) described can include a particular feature, structure, or characteristic, but every embodiment might not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

In general, terminology can be understood at least in part from usage in context. For example, terms, such as "and", "or", or "and/or," as used herein can include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, can be used to describe any feature, structure, or characteristic in a singular sense or can be used to describe combinations of features, structures or characteristics in a plural sense. Similarly, terms, such as "a," "an," or "the," again, can be understood to convey a singular usage or to convey a plural usage, depending at least in part upon context. In addition, the term "based on" can be understood as not necessarily intended to convey an exclusive set of factors and can, instead, allow for existence of additional factors not necessarily expressly described, again, depending at least in part on context.

As used herein, the terms "comprises," "comprising," "includes," "including," or any other variation thereof, are intended to cover a non-exclusive inclusion, such that a process, method, article, or apparatus that comprises a list of elements does not include only those elements but can include other elements not expressly listed or inherent to such process, method, article, or apparatus.

As used herein, "search query" and "query data" may include, for example, without limitation, any data used to search or query one or more databases, data systems, or data storages. The search query or query data may include, but is not limited to, keywords, key phrases, strings, substrings, terms, and codes.

The term "electronic medical record (EMR)" refers to an electronic record comprising patient medical history information. For example, EMRs include, but are not limited to, patient demographic information (e.g., name address, phone number, gender, date of birth, etc.) and medical/health history information (e.g., symptoms, procedures, diagnoses, allergies, conditions, medications, lab/test results, and referral information etc.).

As used herein, "tokens" refer to granular semantic units of data.

As used herein, the term "edit distance" refers to algorithms used to compare two search query strings and determine the minimum number of changes necessary to make one the same as the other.

As used herein, a "machine-learning model" generally encompasses instructions, data, and/or a model configured to receive input, and apply one or more of a weight, bias, classification, or analysis on the input to generate an output. The output may include, for example, an analysis based on the input, a prediction, suggestion, or recommendation associated with the input, a dynamic action performed by a system, or any other suitable type of output. A machine-learning model is generally trained using training data, e.g., experiential data and/or samples of input data, which are fed into the model in order to establish, tune, or modify one or more aspects of the model, e.g., the weights, biases, criteria for forming classifications or clusters, or the like. Aspects of a machine-learning model may operate on an input linearly, in parallel, via a network (e.g., a neural network), or via any suitable configuration.

A machine learning model used herein may be trained and/or used by adjusting one or more weights and/or one or more layers of the machine learning model. For example, during training, a given weight may be adjusted (e.g., increased, decreased, removed) based on training data or input data. Similarly, a layer may be updated, added, or removed based on training data/and or input data. The resulting outputs may be adjusted based on the adjusted weights and/or layers.

The execution of the machine-learning model may include deployment of one or more machine-learning techniques, such as k-nearest neighbors, linear regression, logistical regression, random forest, gradient boosted machine (GBM), support-vector machine, deep learning, text classifiers, image recognition classifiers, You Only Look Once (YOLO), a deep neural network, greedy matching, propensity score matching, and/or any other suitable machine-learning technique that solves problems specifically addressed in the current disclosure. Supervised, semi-supervised, and/or unsupervised training may be employed. For example, supervised learning may include providing training data and labels corresponding to the training data, e.g., as ground truth. Unsupervised approaches may include clustering, classification, principal component analysis (PCA) or the like. K-means clustering or K-Nearest Neighbors may also be used, which may be supervised or unsupervised. Combinations of K-Nearest Neighbors and an unsupervised cluster technique may also be used. Other models for detecting objects in contents/files, such as documents, images, pictures, drawings, and media files may be used as well. Any suitable type of training may be used, e.g., stochastic, gradient boosted, random seeded, recursive, epoch or batch-based, etc.

Certain non-limiting embodiments are described below with reference to block diagrams and operational illustrations of methods, processes, devices, and apparatus. It is understood that each block of the block diagrams or operational illustrations, and combinations of blocks in the block diagrams or operational illustrations, can be implemented by means of analog or digital hardware and computer program instructions. These computer program instructions can be provided to a processor of a general purpose computer to alter its function as detailed herein, a special purpose computer, ASIC, or other programmable data processing apparatus, such that the instructions, which execute via the processor of the computer or other programmable data processing apparatus, implement the functions/acts specified in the block diagrams or operational block or blocks. In some alternate implementations, the functions/acts noted in the blocks can occur out of the order noted in the operational illustrations. For example, two blocks shown in succession can in fact be executed substantially concurrently or the blocks can sometimes be executed in the reverse order, depending upon the functionality/acts involved.

Referring now to the appended drawings, FIG. 1 shows an example system 100 that is implemented with techniques presented herein. For example, the system 100 is used for spell checking and spell correcting. As illustrated in FIG. 1, the system 100 includes a user device 110, a spell check platform 120, a data store 130, and a network 190. The data store 130 may store various types of information. For example, the data store 130 may include correctly spelled words corpus 140, user search history 150, global search history 160, EMR data 170, model dictionaries 180, and a search engine 195. Alternatively, the search engine 195 is implemented outside of the data store 130, and connected to the data store 130 and other components depicted in FIG. 1 via the network 190.

System 100 is implemented on a network 190, allowing for the transmission or sharing of data between each of user device 110, search engine 195, spell check platform 120 and data store 130, which includes one or more of user search history 150, EMR data 170, global search history 160, correctly spelled words corpus 140, and model dictionaries 180, in a network environment. Some or all of the components illustrated in FIG. 1 may be implemented on a cloud platform.

The network 190 may include a wired and/or wireless network that may couple devices so that communications can be exchanged, such as between a server and a user device or other types of devices, including between wireless devices coupled via a wireless network, for example. A network can also include mass storage, such as network attached storage (NAS), a storage area network (SAN), or other forms of computer or machine-readable media, for example. A network can include the Internet, one or more local area networks (LANs), one or more wide area networks (WANs), wire-line type connections, wireless type connections, cellular or any combination thereof. Likewise, sub-networks, which can employ differing architectures or can be compliant or compatible with differing protocols, can interoperate within a larger network. Various types of devices can, for example, be made available to provide an interoperable capability for differing architectures or protocols. As one illustrative example, a router can provide a link between otherwise separate and independent LANs.

Furthermore, devices or user devices, such as computing devices or other related electronic devices can be remotely coupled to a network, such as via a wired or wireless line or link, for example.

In certain non-limiting embodiments, a "wireless network" should be understood to couple user devices with a network. A wireless network can include virtually any type of wireless communication mechanism by which signals can be communicated between devices, between or within a network, or the like. A wireless network can employ stand-alone ad-hoc networks, mesh networks, wireless land area network (WLAN), cellular networks, or the like. A wireless network may be configured to include a system of terminals, gateways, routers, or the like coupled by wireless radio links, or the like, which can move freely, randomly, or organize themselves arbitrarily, such that network topology can change, at times even rapidly.

A wireless network can further employ a plurality of network access technologies, including Wi-Fi, Long Term Evolution (LTE), WLAN, Wireless Router (WR) mesh, or 2nd, 3rd, 4th, 5th generation (2G, 3G, 4G, or 5G) cellular technology, or the like. Network access technologies can allow wide area coverage for devices, such as user devices with varying degrees of mobility, for example.

The user device 110 may include any electronic equipment, controlled by a processor (e.g., central processing unit (CPU)), for inputting information or data and displaying a user interface. A computing device or user device can send or receive signals, such as via a wired or wireless network, or can process or store signals, such as in memory as physical memory states. A user device may include, for example: a desktop computer; a mobile computer (e.g., a tablet computer, a laptop computer, or a notebook computer); a smartphone; a wearable computing device (e.g., smart watch); or the like, consistent with the computing devices shown in FIG. 7.

The user device 110 is used by a user, e.g., a patient. User device 110 is configured to input a search query, which is received by the search engine 195. The user device 110 displays a suggested search query which includes an alternative (e.g., correct) spelling of the original search query input by the user. In some examples, a user is prompted to select the suggested search query displayed on the user device 110. User device 110 is configured to display search results associated with the input search query or a suggested search query selected with user device 110.

The spell check platform 120 is a platform with multiple interconnected components. The spell check platform 120 provides certain modules, databases, user interfaces, and/or the like for performing certain tasks, such as data processing and/or analysis tasks as described in greater detail with respect to FIG. 2. For example, the spell check platform 120 performs the method illustrated in FIG. 3 and uses the spell corrector models illustrated in FIGS. 4-5 as well as the model selector illustrated in FIG. 6.

The data store 130 may include one or more non-volatile memory computing devices that may store data in data structure, databases, and/or the like. Data in the data store 130 is stored in the correctly spelled words corpus 140, the user search history 150, the global search history 160, the EMR data 170, and the model dictionaries 180.

The correctly spelled words corpus 140 stores a collection of correctly spelled words. Correctly spelled words that are collected and stored in the correctly spelled words corpus 140 are retrieved from a variety of sources, including various open source websites (e.g., Wikipedia®) and databases. In some examples, correctly spelled words are collected from medical databases and online medical dictionaries. For example, correctly spelled words herein are collected from dictionaries such as MedDRA (Medical Dictionary for Regulatory Activities), which includes information about medical terminology and may be used for coding adverse events, clinical signs and symptoms, procedures, investigations, indications, and medical and social histories; SNOMED CT (Systematized Nomenclature of Medicine-Clinical Terms), which includes clinical terminology; and the WHO (World Health Organization) Drug Dictionary, a dictionary that includes medicinal product information.

In some embodiments, the correctly spelled words corpus 140 includes medical abbreviations, medical provider names, pharmacy names, drug names, drug brands, medical procedure names, medical occupations, and clinical codes/terms (e.g., from International Classification of Diseases (ICD)-9, ICD-10, and SNOMED CT), as well as any other healthcare or medical terminology. Each word in the correctly spelled words corpus 140 is stored together with its frequency of appearing in a search query. In some embodiments, the correctly spelled words corpus 140 stores a collection of correctly spelled words and their corresponding search query input frequencies.

User search history 150 is a data storage for storing the search history data associated with the user device 110. The user search history 150 stores the search history (e.g., prior search queries) for each query session of a user using user device 110. For example, any search query that is input via a user interface of user device 110 is stored in the user search history 150. For each query session, in which a new search query is input or a suggested search query is selected with the user device 110, the search query is broken into individual words or terms. A frequency of each search query term stored in the user search history 150 is computed. The search query term frequencies for words that are correctly spelled in the user search history 150 are used for storing with the corresponding words in the correctly spelled words corpus 140.

The user search history 150 stores forced correction mapping data, which maps misspelled query words to correctly spelled words from the correctly spelled words corpus 140. A forced correction module of the spell check platform 120 associates certain misspelled words entered as a search query input with correctly spelled words from the correctly spelled words corpus 140 and each correlation between a misspelled word and a correctly spelled word is stored in the user search history 150. The forced correction mapping data that is stored in the user search history 150 is based on sequential search query inputs that occur in a single user session using the user device 110.

Global search history 160 is a data storage for storing the search history data (e.g., prior search queries) associated with all user devices on the network 190. While FIG. 1 depicts the user device 110, the global search history 160 stores prior search query data for a plurality of users of the search engine 195. The global search history 160 stores the search history data associated with the user device 110 as described with respect to the user search history 150 together with the search history data associated with all other user devices that utilize the search engine 195. The prior search query data stored in the global search history 160 associates each word from a search query with a corresponding frequency of occurrence in the search queries of all users using the search engine 195. The search query term frequencies for words that are correctly spelled in the global search history 160 are used for storing with the corresponding words in the correctly spelled words corpus 140. The search query term frequencies for words that are correctly spelled in the global search history 160 are also used in the model selector module of the spell check platform 120, which is described in greater detail with respect to FIGS. 2 and 6. In some examples, the global search history 160 stores user search history corresponding to a particular time period. For example, the global search history 160 stores search history data for search queries occurring within at least 5 years.

EMR data store 170 is a data storage or a database storing EMRs associated with one or more patients. In some examples, other health data associated with a patient such as a clinician's notes and/or recordings, other point-of-care documentation, and discharge documentation are stored in EMR data store 170. The EMR data store 170 stores EMR data for the user associated with the user device 110. For example, the EMR data store 170 stores data for one or more previous diagnoses, one or more previous medical procedures, and/or one or more previous pharmaceutical claims.

Model dictionaries 180 include a plurality of dictionaries (e.g., lexicons) each of which is used by a spell corrector model from the plurality of spell corrector models used in the spell check platform 120. Each of the model dictionaries 180 comprises a different collection of words depending on the associated spell corrector model. Some of the model dictionaries 180 include a collection of words and/or terms that are associated with user data. For example, one model dictionary from the model dictionaries 180 is based on data from the user history 150. Another model dictionary from the model dictionaries 180 is based on data from the EMR data store 170. Another model dictionary from the model dictionaries 180 is based on the global search history 160. Model dictionaries 180 that are based on either the user search history 150 or the EMR data store 170 include personal data (e.g., prior search history or medical history) for a user, such as the user associated with the user device 110. In addition, some model dictionaries 180 include a collection of words imported from various external sources. For example, some model dictionaries 180 are external dictionaries. These external dictionaries include general dictionaries and specialized dictionaries (e.g., medical dictionaries).

The search engine 195 receives search queries from user devices on network 190, such as the user device 110. The search engine 195 queries a search index or database (not shown) for the search query input via a user device, such as user device 110. The search engine 195 also transmits search results that are generated based on the search query to the user device 110.

Figure 2:
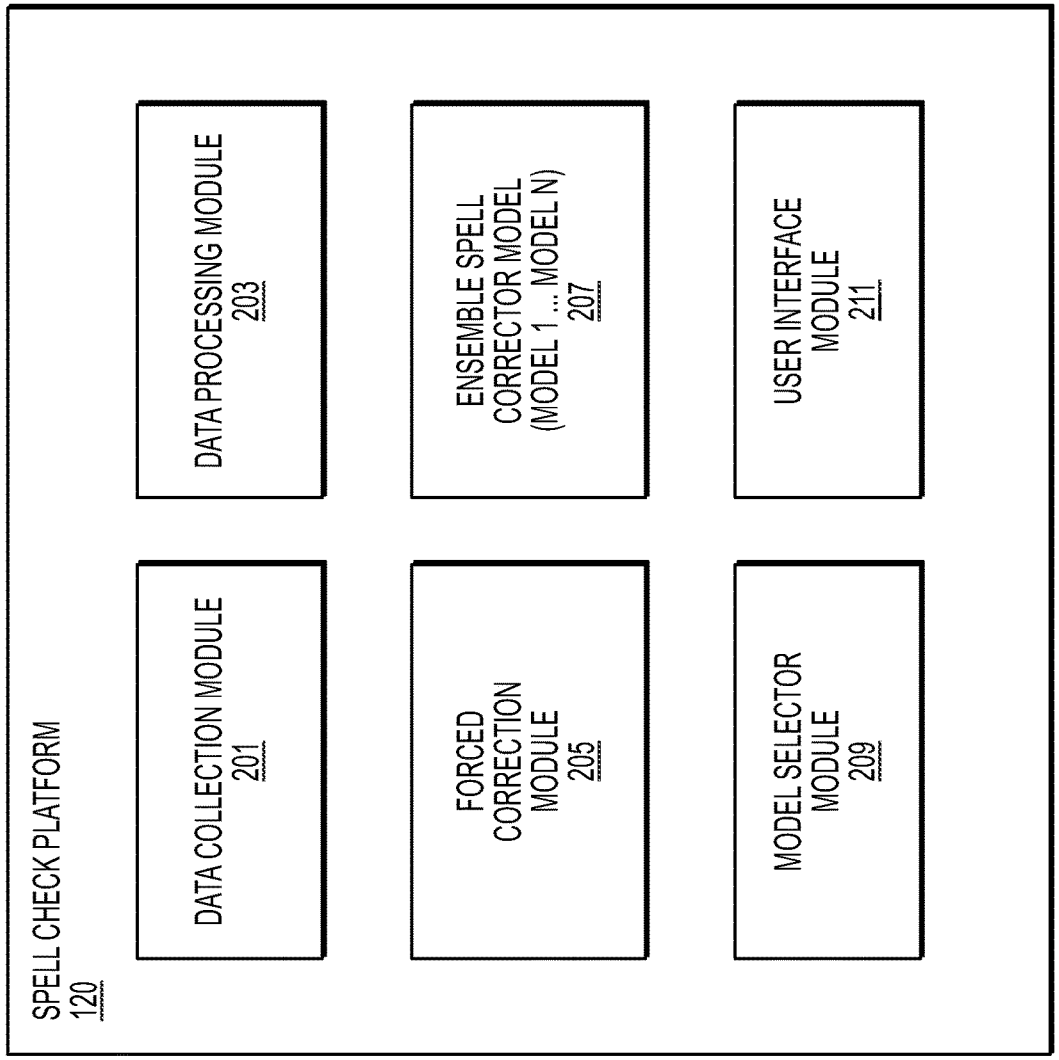
FIG. 2 depicts a diagram of the components of an example spell check platform, according to one or more embodiments.

FIG. 2 depicts a diagram of the components of spell check platform 120. By way of example, spell check platform 120 includes one or more components for processing a search query, determining if the search query is spelled correctly, using a plurality of spell corrector models to provide a suggested search query for each of the models when the search query is determined to contain a misspelling, and selecting an optimal suggested search query determined using one of the spell corrector models from the plurality of spell corrector models. It is contemplated that the functions of these components may be combined in one or more components or performed by other components of equivalent functionality. Spell check platform 120 may include one or more servers, intelligent networking devices, computing devices, components, and corresponding software for processing a search query, determining if the search query is spelled correctly, using a plurality of spell corrector models to provide a suggested search query for each of the models when the search query is determined to contain a misspelling, and selecting an optimal suggested search query determined using one of the spell corrector models from the plurality of spell corrector models. In addition, it is noted that spell check platform 120 may be a separate entity of system 100. In an example embodiment, spell check platform 120 comprises data collection module 201, data processing module 203, forced correction module 205, ensemble spell corrector model 207, model selector module 209, and user interface module 211, or any combination thereof.

Data collection module 201 receives via the network 190 search queries input by users. For example, the data collection module 201 receives search queries input using user device 110. The data collection module 201 may also receive search queries input using other user devices. In one embodiment, the data collection module 201 receives the search queries received by the search engine 195.

Data collection module 201 is programmed to collect, in real-time, historical information, contextual information, or a combination thereof pertaining to the users, so that identification, analysis, response, monitoring, and control are performed using the most recent data. For example, the data collection module 201 collects data from the user search history 150, the global search history 160, and the EMR data store 170. The data collection module 201 also collects data associated with the correctly spelled words corpus 140. In one example embodiment, data collection module 201 includes various software applications, e.g., data mining applications in Extended Meta Language (XML) that automatically search for and return relevant information pertaining to a user. In one embodiment, data collection module 201 collects, in real-time, correctly spelled words and their corresponding query frequencies from the user search history 150 and/or the global search history 160. In one embodiment, data collection module 201 collects, in real-time, health data or EMR data associated with a user, e.g., a patient, from EMR data store 170. The data collection module 201 may also periodically collect new correctly spelled words from a variety of sources to update the correctly spelled words corpus 140 and/or the model dictionaries 180.

In one embodiment, data collection module 201 parses and arranges the data into a common format that can be easily processed by other modules and platforms. The data collection module 201 includes a preprocessing component for preprocessing the data received. Preprocessing according to the present disclosure includes tokenization and normalization of data. Tokenization identifies and separates data received into tokens. In aspects of the present disclosure, preprocessing (e.g., tokenization) includes breaking down text from the data into individual words and other components of text (e.g., punctuation). For example, a search query that is received which includes phrases (i.e. multiple words) is broken down into individual words.

A preprocessing component of the data collection module 201 also normalizes data. Normalization includes, but is not limited to, lowercasing of text, stripping of punctuation, expansion of common abbreviations to a proper phrase, and replacement of non-ASCII characters. In some examples herein, the data collection module 201 includes running data through a preprocessor for tokenization and/or normalization. For example, a preprocessor of data collection module 201 performs the steps listed in Table 1. A search query input received may be preprocessed according to the steps in Table 1.

TABLE 1

Preprocessing Steps

| | |
|---|---|
| a. | Lower case |
| b. | Remove non-ASCII |
| c. | Replace ",[ ]:; +&" with space |
| d. | Replace "'s" with space |
| e. | Replace "'" with space |
| f. | Replace "." with space |
| g. | Replace "." with space |
| h. | Replace "dr." with "dr" |
| i. | Replace "st." with "saint" |

Data processing module 203 processes data collected and preprocessed by data collection module 201 to determine whether a search query that is received from a user is spelled correctly. The data processing module 203 searches and/or scans the correctly spelled words corpus 140 to determine if the search query (e.g., search query terms) exists therein. Search query terms that are determined to exist in the correctly spelled words corpus 140 are recognized as being correctly spelled. Search query terms that are not found within the correctly spelled words corpus 140 are recognized as being misspelled and in need of correction. The data processing module 203 also computes the frequency of each word in the search queries received. In particular, the data processing module 203 determines the frequency of each correctly spelled word from the search queries associated with a single user and/or a plurality of users. For example, data processing module 203 determines the frequency of each correctly spelled word within the user search history 150 and the global search history 160.

The data processing module 203 also encodes the data collected and preprocessed by data collection module 201. For example, the data processing module 203 encodes EMR data associated with a user. The EMR data, which may be encoded, includes previous diagnoses, previous medical procedures, and previous pharmaceutical claims. The data processing module 203 utilizes multi-hot encoding or a latent dimension of an autoencoder. The EMR data is encoded to generate embeddings, referred to herein as claims embeddings, for a spell corrector model of the present disclosure. The data processing module 203 also processes data to create user-based dictionaries for the model dictionaries 180. For example, a model dictionary 180 is created to include claims embeddings associated with a user. Another model dictionary 180 may be created based on the user search history 150.

Forced correction module 205 determines if a similarity exists between words of a search query that do not exist in the correctly spelled words corpus 140 (e.g., misspelled words) and any of the correctly spelled words from the correctly spelled words corpus 140. The forced correction module 205 accesses the user search history 150. In particular, the forced correction module 205 analyzes the data in the user search history 150 associated with a single user search session. In one embodiment, a single user search session includes the input of successive search queries by the user in the same search session. The forced correction module 205 analyzes the first search query input by the user, followed by conducting an analysis of subsequent search queries for a session. If a search query term from the session is determined to have a correct spelling, the correctly spelled search query term is compared with a search query term from the session that is determined to be misspelled. In some examples, an initial search query during a search session is determined to be misspelled and may not be found in the correctly spelled words corpus 140, while a subsequent search query from the same search session is determined to be correctly spelled. These queries may be compared.

The forced correction module 205 applies an edit distance algorithm to assess the similarity between query terms in the same search session. For example, the forced correction module 205 computes an edit distance between a first search query and a subsequent search query determined to be correctly spelled. The edit distance is measured between successive search queries. In some examples, the edit distance is based on a Levenshtein distance. In other examples, the edit distance is based on another suitable edit distance algorithm. The forced correction module 205 associates a misspelled search query with a correctly spelled search query from a search session when the edit distance is less than or equal to a threshold. The forced correction module 205 generates a forced correction mapping, which maps a misspelled search query term to a correctly spelled word when the edit distance between the pair is less than a threshold value. The forced correction mapping refers to a data structure that maps misspelled search query terms to correctly spelled search query terms. For example, if the edit distance is below a threshold, the forced correction module 205 maps a first search query from a search session as an input of a forced correction function and a subsequent search query from the session as an output. In some examples, an edit distance of less than 3, such as 2 or less, satisfies the threshold requirements necessary for mapping according to the present disclosure.

The forced correction mapping generated by the forced correction module 205 includes search query terms that do not exist in the correctly spelled words corpus 140 as the input. The output includes search query terms that exist in the correctly spelled words corpus 140. The forced correction mapping data associates a misspelled search query with a corresponding correctly spelled search query. The forced correction mapping may only be stored when the input is a search query that does not exist in the correctly spelled words corpus 140 and the output is a search query that does exist in the correctly spelled words corpus 140. Forced correction module 205 stores all valid forced correction mapping data. In some examples, the forced correction mapping data is stored in the data store of the user search history 150. In at least one example, the forced correction mapping data is stored in a different data store than the data store of user search history 150.

Forced correction module 205 also modifies the spelling of a search query received from a user based on the forced correction mapping data. The forced correction module 205 forces or causes a search query, such as a search query that is recognized as being misspelled, to be spelled a certain way. By way of example, a forced correction mapping is generated when a user inputs a search query such as "ofthalmology", followed by a subsequent search query of "ophthalmology". In this particular example, the first search query is not found in the correctly spelled words corpus 140, while the second search query is found in the correctly spelled words corpus 140. An edit distance (e.g., Levenshtein distance) between the two queries is below 3. Given that there is a small edit distance, a forced correction mapping maps an input of the misspelled search query "ofthalmology" to an output of the correctly spelled search query "ophthalmology". In this case, "ofthalmology" which is not found in the correctly spelled words corpus 140 may always be associated with "ophthalmology", which is found in the correctly spelled words corpus 140. Thus, "ophthalmology" is recognized as the correct spelling associated with "ofthalmology". Once the forced correction mapping data for the search query term "ofthalmology" has been stored, the forced correction module 205 causes "ofthalmology" to be spelled as "ophthalmology" each time that "ofthalmology" is input as a search query from the user. In some examples, the forced correction module 205 automatically updates or edits the spelling of a misspelled search query to achieve the spelling of the associated correctly spelled search query based on the forced correction mapping data.

Figure 6:
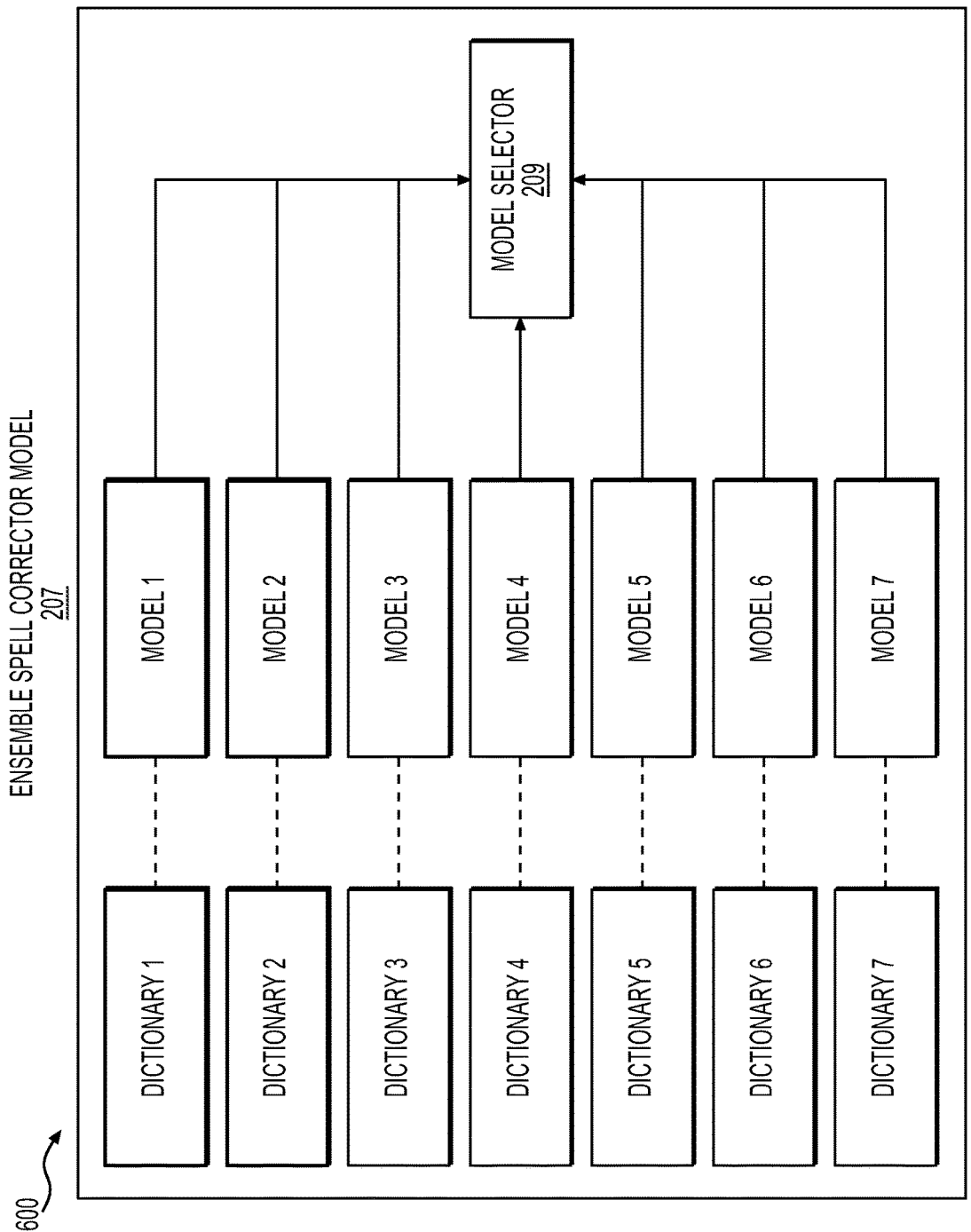
FIG. 6 depicts a block diagram of an example model selection framework, according to one or more embodiments.

An ensemble spell corrector model 207, which includes a plurality of spell corrector models, may also be a component of the spell check platform 120. For example, a plurality of spell corrector models are ensembled to form ensemble spell corrector model 207. The ensemble spell corrector model 207 may also be referred to herein as a plurality of spell corrector models 207. The ensemble spell corrector model 207 generates a plurality of suggested search queries based on lexicon data. The plurality of spell corrector models 207 comprise N number of (spell corrector) models where N is an integer greater than one. As shown in FIG. 2, the ensemble spell corrector model 207 includes a plurality of spell corrector models ranging from a first model (Model 1) to an Nth model (Model N). The ensemble spell corrector model 207 comprises at least two spell corrector models. For example, the plurality of spell corrector models of the ensemble spell corrector model 207 include from 2 to 20 spell corrector models, from 3 to 15 spell corrector models, from 5 to 10 spell corrector models, or from 4 to 8 spell corrector models. In some examples herein, the ensemble spell corrector model 207 includes at least 5 spell corrector models. As shown in FIG. 6, an example spell corrector model 207 includes 7 (spell corrector) models.

Each of the spell corrector models from the ensemble spell corrector model 207 uses a different dictionary in determining a suggested search query as a potential alternative to the search query input. Some spell corrector models of the ensemble spell corrector model 207 use dictionaries based on the personal information of the same user who enters the search query input. Some spell corrector models of the ensemble spell corrector model 207 use external dictionaries. In some examples, a spell corrector model of the ensemble spell corrector model 207 uses a specialized dictionary, such as a medical dictionary. In some examples, a spell corrector model of the ensemble spell corrector model 207 uses a dictionary based on the search history of a plurality of users using the search engine 195.

The ensemble spell corrector model 207 may also include different spell corrector models. For example, different types of models are ensembled in the spell corrector model 207. Some of the spell corrector models are based on an edit distance algorithm. At least one of the spell corrector models from the plurality of spell corrector models 207 may be a machine learning model. For example, a spell corrector model from the plurality of spell corrector models is a trained machine learning model. A spell corrector model herein includes a transformer-based component.

In one embodiment, the ensemble spell corrector model 207 receives a search query that is not listed in the correctly spelled words corpus 140 and determines a plurality of suggested search queries. Each of the plurality of suggested search queries is determined using a spell corrector model from the plurality of spell corrector models 207. Each suggested search query from the plurality of suggested search queries is based on a different dictionary that is used by each spell corrector model from the ensemble spell corrector model 207 to determine a suggestion. In some examples, each spell corrector model from the plurality of spell corrector models 207 generates a different suggested search query.

Model selector module 209 selects a suggested search query from the plurality of suggested search queries determined using the ensemble spell corrector model 207. After outputs (e.g., suggested search queries) are generated by spell corrector models from the ensemble spell corrector model 207, the model selector 209 performs an analysis to select a suggested search query determined by one of the spell corrector models from the plurality of spell corrector models 207. The model selector 209 selects the optimal suggested search query from a plurality of suggested search queries, each determined using a model from the ensemble spell corrector model 207. In order to make a selection, the model selector 209 analyzes the global search history 160 to determine how frequently each of the suggested search queries occurred within the search history. The model selector 209 is also configured to select the optimal suggested search query based on a weightage of each of the spell corrector models from the ensemble spell corrector model 207.

User interface module 211 enables a presentation of a graphical user interface (GUI) in user device 110. User interface module 211 may comprise a variety of interfaces, for example, interfaces for data input and output devices, referred to as I/O devices, storage devices, and the like. The user interface module 211 displays search results generated by a user search query. The user interface module 211 also displays a suggested search query selected by the model selector 209.

Figure 3:
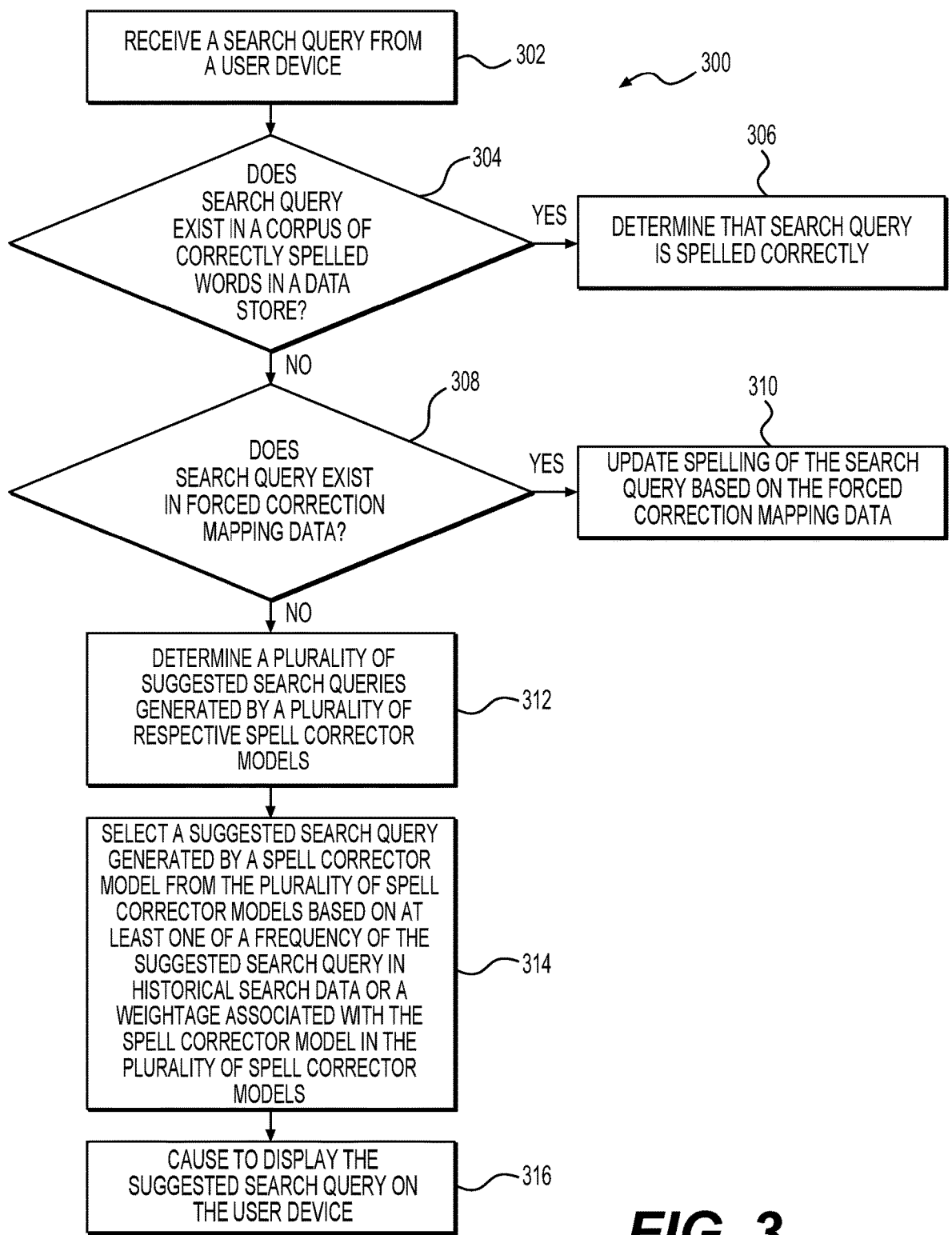
FIG. 3 depicts a flowchart of an example process for spell checking, according to one or more embodiments.
Figure 7:
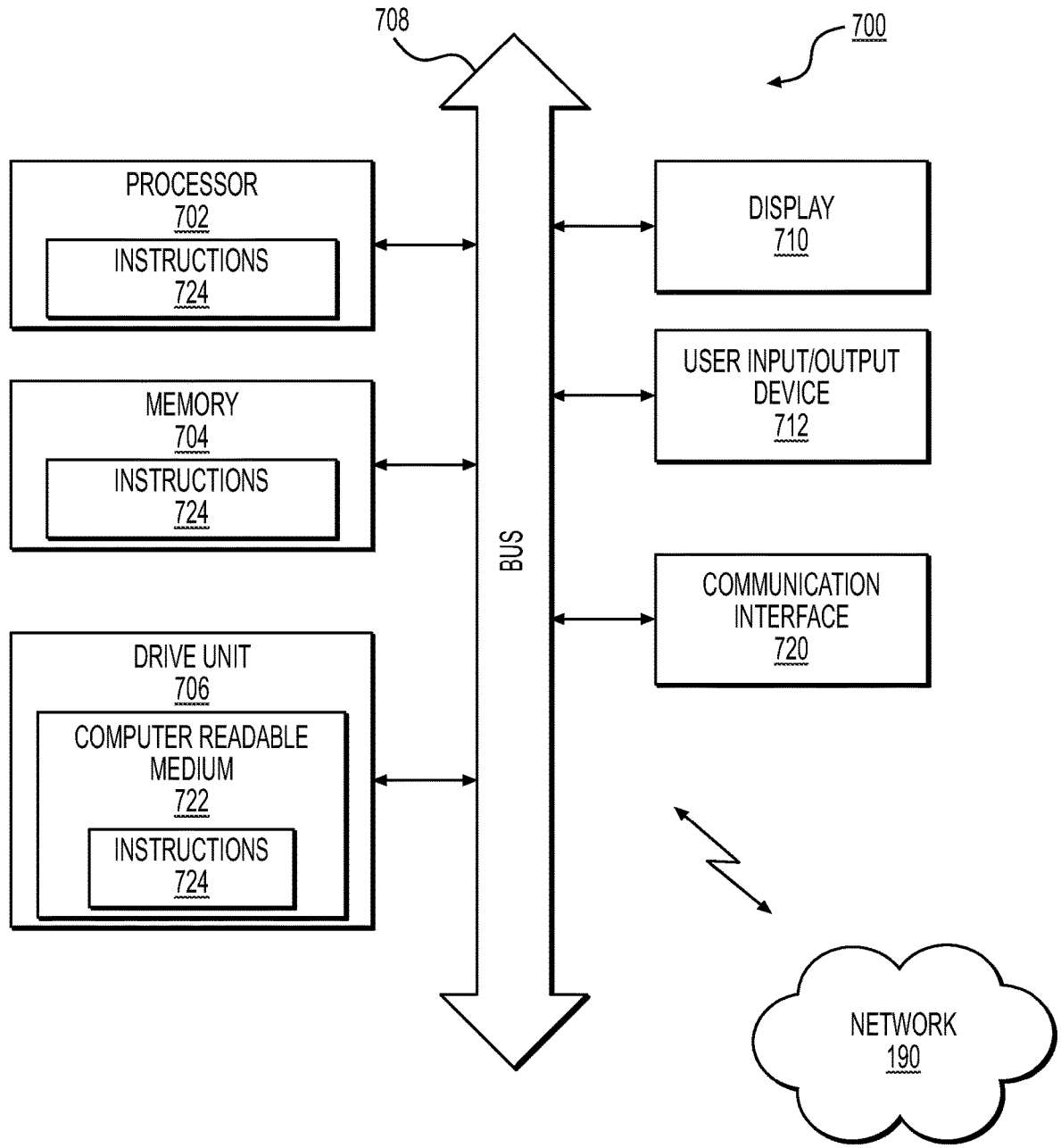
FIG. 7 illustrates an implementation of a computer system that may execute techniques presented herein.

FIG. 3 shows a flowchart of an example process 300 for spell checking a search query. In various embodiments, spell check platform 120 and/or any of modules 201-211 may perform one or more portions of process 300 and may be implemented in, for instance, a chip set including a processor and a memory as shown in FIG. 7. As such, spell check platform 120 and/or any of modules 201-211 provide means for accomplishing various parts of process 300, as well as means for accomplishing embodiments of other processes described herein in conjunction with other components of system 100. Although process 300 is illustrated and described as a sequence of steps, it is contemplated that various embodiments of process 300 may be performed in any order or combination and need not include all of the illustrated steps.

In step 302, the spell check platform 120 receives a search query (e.g., query data) from a user device associated with a user. For example, a user inputs the search query via the user device 110. Once the spell check platform 120 receives the search query (e.g., user search query) from the user device, the spell check platform 120 preprocesses the search query. For example, the search query is broken down into individual words and subjected to preprocessing, which includes lowercasing of text, stripping of punctuation, expansion of common abbreviations to a proper phrase, and replacement of non-ASCII characters. In some examples, the search query is a medical or healthcare related query. For example, the search query includes one or more terms relating to a health condition, medical occupation, prescription, and/or a medical treatment.

In step 304, the spell check platform 120 determines if the search query received in step 302 exists in the correctly spelled words corpus 140. The correctly spelled words corpus 140 includes a collection of correctly spelled queries. Each correctly spelled word from the correctly spelled words corpus 140 is stored with a corresponding frequency of appearing in a search. In response to determining that the search query input by the user exists in the correctly spelled words corpus 140, the spell check platform 120 proceeds to step 306. In step 306, the spell check platform 120 determines that the search query received in step 302 is spelled correctly. After determining that the search query is correctly spelled in step 306, the search query is used to query a database (e.g., a healthcare database).

In response to determining that the search query input does not exist in the correctly spelled words corpus 140 in step 304, the spellcheck platform 120 proceeds to step 308. In step 308, the spell check platform 120 determines whether the search query exists in forced correction mapping data. Forced correction mapping data includes a mapping of a misspelled search query term to a correctly spelled word. For example, the forced correction mapping data is generated based on a prior search session of the user. The spell check platform 120 generates the forced correction mapping data by: receiving a first search query from the user in a session; receiving a subsequent search query from the user in the session; determining that the subsequent search query exists in the corpus of correctly spelled words; computing an edit distance between the first search query and the subsequent search query; associating the first search query with the subsequent search query when the edit distance is less than a predefined threshold; and storing the association. In some examples, the edit distance is a Levenshtein edit distance and the predefined threshold is less than or equal to 3.

In response to determining that the search query exists in the forced correction mapping data, the spell check platform 120 proceeds to step 310. In step 310, the spell check platform 120 updates the spelling of the search query based on the stored forced correction mapping data. Updating the spelling of the search query includes replacing misspelled search query terms from the search query input by the user with the associated correctly spelled terms from the forced correction mapping data. In some examples, step 310 includes automatically performing insertions, deletions, replacements, and/or transpositions for the misspelled search query in order to output the associated correctly spelled words. After updating (e.g., correcting) the spelling of the search query in step 310, the search query is used to query a database (e.g., a healthcare database).

In response to determining that the search query does not exist in the forced correction mapping data in step 308, the spell check platform 120 proceeds to step 312. For example, spell check platform 120 proceeds to step 312 when the search query that was not found in the correctly spelled words corpus 140 has no associated mapping in the forced correction mapping data. The spell check platform 120 may also proceed to step 312 when there is no stored forced correction mapping data.

In step 312, the spell check platform 120 determines a plurality of suggested search queries generated by a plurality of respective spell corrector models 207 (ensemble spell corrector model 207). In some examples, the plurality of spell corrector models 207 includes at least five spell corrector models. For example, the ensemble spell corrector model 207 includes a total of seven spell corrector models. In some examples, at least two of the spell corrector models from the ensemble spell corrector model 207 are based on data associated with the user who input the search query in step 302. For example, two of the spell corrector models use personal data of the user to determine suggested search queries. The personal data associated with the user includes prior search history and/or EMR data (e.g., one or more prior pharmaceutical claims, one or more of a previous diagnosis, and/or one or more of a previous medical procedure). Each of the spell corrector models from the ensemble spell corrector model 207 uses a different dictionary to determine a suggested search query. At least one spell corrector model is a trained machine learning model. The individual spell corrector models used in step 312 are described in greater detail with respect to FIGS. 4-6.

In step 314, model selector 209 selects a suggested search query generated by a spell corrector model from the plurality of spell corrector models 207. The selection of the suggested search query is based on at least one of a frequency of the suggested search query in the global search history 160 or a weightage associated with the spell corrector model in the plurality of spell corrector models 207 (or weightage associated with each spell corrector model in the plurality of spell corrector models 207). For example, the suggested search query that occurs more frequently in the global search history 160 is selected by the model selector 209. When the suggested search queries do not appear in the global search history 160, the model selector 209 selects a suggested search query based on a predefined weightage of the associated spell corrector model relative to the other spell corrector models. The model selector 209 is described in greater detail with respect to FIG. 6. In some examples, the model selector 209 evaluates the frequency of the suggested search queries in the global search history 160 prior to making a selection based on the weightage of the model.

In step 316, the spell check platform 120 causes the suggested search query selected in step 314 to be displayed on user device 110. In some examples, the user is prompted to select the suggested search query. For example, a wireframe of the database that the user intends to search informs the user that their search did not return any results and provides a link for selecting the suggested search query instead.

Figure 4:
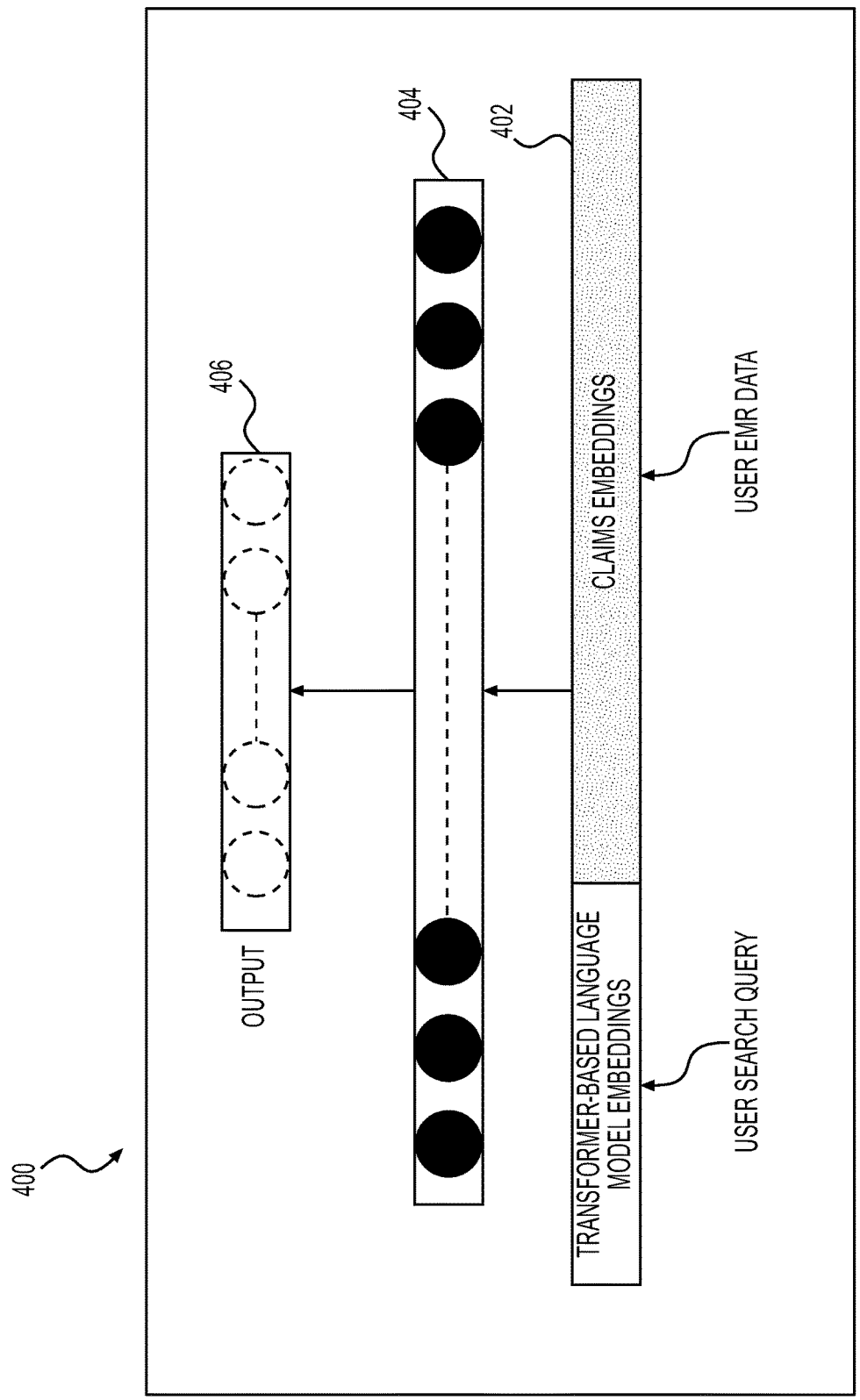
FIG. 4 depicts an example spell corrector model, according to one or more embodiments.

FIG. 4 illustrates a diagram of an example spell corrector model. Spell corrector model 400 as shown in FIG. 4 may be included in the ensemble spell corrector model 207 of the spell check platform 120. For example, the spell corrector model 400 is used in the spell check process 300 as one of the spell corrector models from a plurality of spell corrector models for determining a suggested search query. The spell corrector model 400 may also correspond to model 2 shown in FIG. 6.

The spell corrector model 400 may be a trained machine learning model, used in determining a suggested search query based on lexicon data as an alternative to the original search query input by a user, which is not found in a correctly spelled words corpus. For example, the spell corrector model 400 is a feed-forward neural network. In one embodiment, the spell corrector model 400 is a two layer feed-forward network, such as a multilayer perceptron (MLP). The spell corrector model 400 processes EMR data associated with the user who inputs the search query in step 302 of process 300 in conjunction with the search query to determine a suggested search query based on contextual data. The spell corrector model 400 includes a concatenation component 402, a feed-forward component 404, and a softmax component 406.

The concatenation component 402 is based on the EMR data associated with the user and the misspelled search query input by the user. Prior to concatenation, the respective data is processed to obtain embeddings. For example, the search query of the user is input into a transformer-based language model, such as a Generative Pretrained Transformer (GPT) or GPT2. In some examples, a search query of the user is passed through a Bidirectional Encoder Representations and Transformers (BERT) model after being pre-processed. The BERT model is pre-trained using a corpus or a dataset for language modeling such as the one billion words benchmark. Passing the pre-processed search query through a transformer-based language model (e.g., pre-trained BERT) generates an output embedding layer. The output (e.g., embeddings) from the transformer-based language model is used in the concatenation component 402.

Claims embeddings may also be used in the concatenation component 402. The claims embeddings are obtained by encoding EMR data associated with the user. As previously discussed, the EMR data of the user includes previous diagnoses, previous procedures, and previous pharmaceutical claims. EMR data associated with the user is retrieved from the EMR data store 170 and encoded to generate a claims embedding. Encoding techniques including, but not limited to, multi-hot encoding and a latent dimension of an autoencoder are used to encode the EMR data and generate claims embeddings.

Once the transformer-based language model embeddings associated with the user search query and the claims embeddings associated with the user EMR data have been separately obtained, the transformer-based language model embeddings and the claims embeddings are concatenated in the concatenation component 402 of the spell corrector model 400 to generate a concatenated embedding. The concatenation component 402 containing the concatenated embedding is an input layer of the spell corrector model 400. For example, the concatenated embedding generated in the concatenation component 402 is then fed as an input to the feed-forward component 404.

The feed-forward component 404 includes one or more feed-forward layers. In some examples, the feed-forward component 404 includes two feed-forward layers. The feed-forward layers of the feed-forward component 404 are utilized to generate a feed-forward output. The feed-forward output includes a suggested search query that is correctly spelled. The resulting feed-forward output from the feed-forward component 404 is applied to a softmax component 406 to generate a measure (e.g., a probability) that indicates whether a suggested search query is correctly spelled in the context of the input layer, which is a concatenation of the transformer-based language model embeddings associated with the user search query and the claims embeddings associated with the user EMR data. For example, a suggested search query with the highest probability is output from the spell corrector model 400.

As discussed herein, the spell corrector model 400 may be a trained machine learning model. For example, the spell corrector model 400 is trained based on a training data set. The training data includes a plurality of query samples and corresponding query spellings. The corresponding query spellings are queries that have a correct spelling. Each query sample includes transformer-based language model embeddings and the claims embeddings for a user.

One or more operations are performed on the associated training transformer based language embeddings and training claims embeddings to generate specific input associated with the samples for provision to the spell corrector model 400 during a training process. For example, for each of the plurality of query samples, a training transformer-based language model embedding is received from a pre-trained transformer-based language model (e.g., BERT model). Additionally, for each of the plurality of samples, training EMR data is encoded to generate a training claims embedding. One or more techniques can be used individually or in combination to encode the training EMR data. For example, multi-hot encoding, a latent dimension of an autoencoder and/or dimension reduction techniques, such as principal component analysis (PCA), can be used to encode the training EMR data.

In some examples, the training embedding received from a transformer-based language model and the training claims embedding for each sample are then concatenated or otherwise joined to generate a training concatenated embedding for the respective query sample that is provided as input to the spell corrector model 400 for the training. The spell corrector model 400 is trained to output a probability distribution indicating a likelihood that a suggested search query is correctly spelled. The output is compared with the corresponding correct spelling for the query sample to determine an error which is then back-propagated through the model to adjust the values of the variables. This process is repeated for at least the portion of the samples until a determined loss or error is below a predefined threshold. Once trained, the spell corrector model 400 (e.g., trained spell corrector model 400) is stored for subsequent use.

Figure 5:
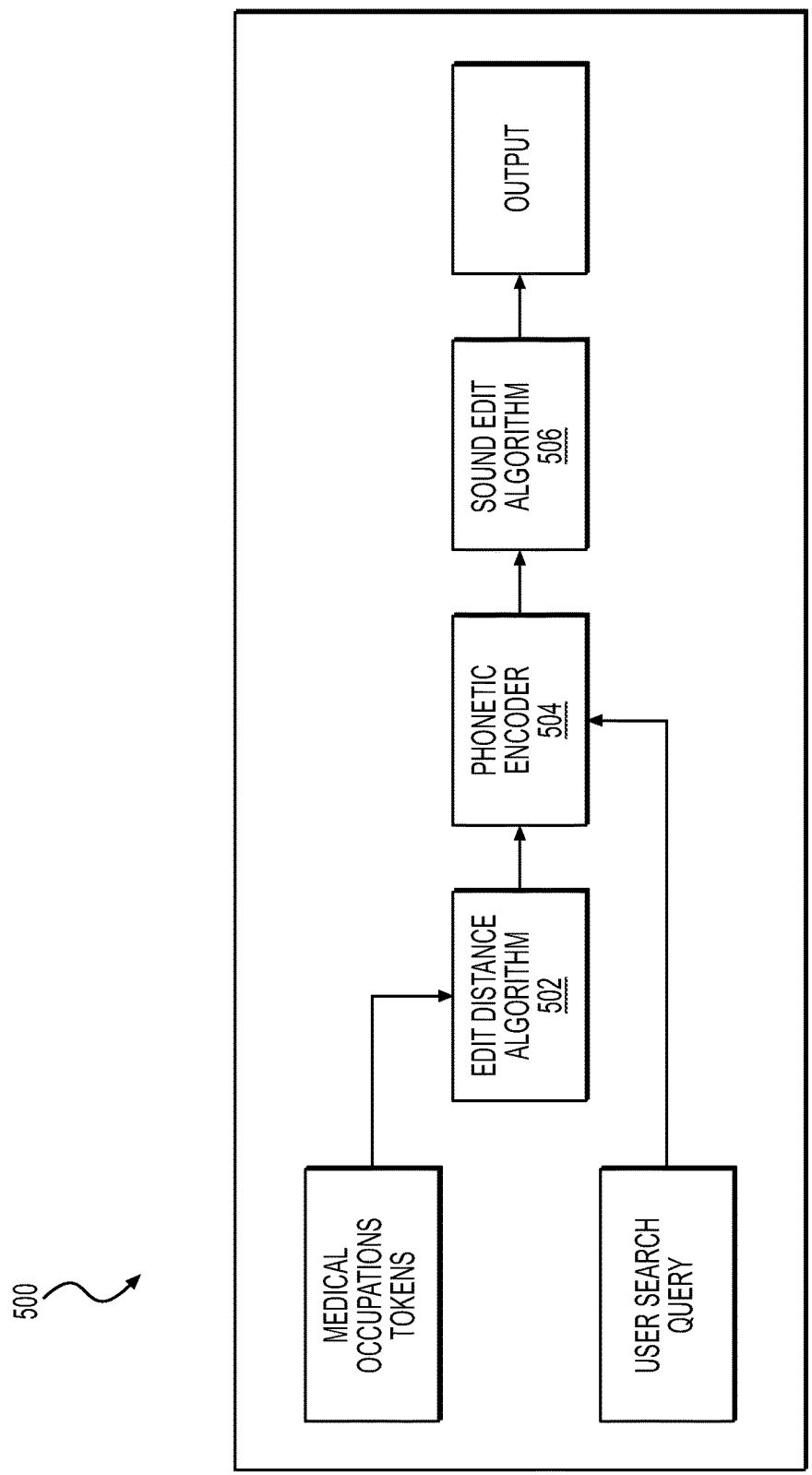
FIG. 5 depicts another example spell corrector model, according to one or more embodiments.

FIG. 5 illustrates a diagram of an example spell corrector model of the present disclosure. Spell corrector model 500 as shown in FIG. 5 may be included in the ensemble spell corrector model 207 of the spell check platform 120. For example, the spell corrector model 500 is used in the spell check process 300 as one of the spell corrector models from a plurality of spell corrector models for determining a suggested search query. The spell corrector model 500 may also correspond to model 5 shown in FIG. 6. In particular, the spell corrector model 500 includes a phonetic encoding component, which may be useful in scenarios where the user search query is spelled according to how it sounds, but is not found in the correctly spelled words corpus 140. For example, a user inputs a search query (e.g., peal) which is a homophone of a word (e.g., pill) that is found in the correctly spelled words corpus 140.

The spell corrector model 500 includes an edit distance algorithm 502, a phonetic encoder 504, and a sound edit distance algorithm 506. In one embodiment, the spell corrector model 500 uses a model dictionary (e.g., a model dictionary 180) based on medical occupations tokens. For example, the data collection module 201 of the spell check platform 120 collects a corpus of medical occupations and related terminology. The medical occupation inputs received are tokenized into medical occupations tokens. The resulting medical occupations tokens dictionary is used by the spell corrector model 500 in determining a suggested search query that serves as a potential spell correction candidate for the original search query input by a user.

As shown in FIG. 5, the spell corrector model 500 receives a user search query. For example, the spell corrector model 500 receives a user search query that is not found in the correctly spelled words corpus 140. The edit distance algorithm 502 is used to determine potential spell correction candidates that may form a suggested search query for replacing the user search query. The potential spell correction candidates is referred to herein as suggested search query candidates. The edit distance algorithm 502 computes the edit distance between the user search query and the terms from the medical occupations tokens dictionary. In some examples, the edit distance algorithm 502 is a Levenshtein distance. The suggested search query candidates (e.g., a list of candidates) are determined when an edit distance between a medical occupation token and the user search query is below a threshold. The suggested search query candidates that are based on medical occupations tokens are determined for an edit distance of 5 or less. In some examples, model 7 shown in FIG. 6, and described in further detail with respect to FIG. 6, is used for the edit distance algorithm 502.

The suggested search query candidates that are determined by using the edit distance algorithm 502 are output from the edit distance algorithm 502 and input into the phonetic encoder 504. The phonetic encoder 504 converts words into their phonetic equivalent. For example, the phonetic encoder 504 receives a term (e.g., a suggested search query candidate) and then encodes the term to produce a corresponding sound code. Once a sound code is generated, the sound code is output from the phonetic encoder 504. Examples of phonetic encoders include Exact Match, Metaphone, Double Metaphone, Soundex, Caverphone, Caverphone 2.0, and Daitch-Mokotoff. In some examples, the phonetic encoder 504 is a Caverphone (e.g., Caverphone 2.0) encoder. In addition to encoding the suggested search candidates output from the edit distance algorithm 502, the phonetic encoder 504 may also encode the user search query. Thus, the phonetic encoder 504 generates sound code outputs for both the user search query (e.g., the original user search query) and the suggested search query candidates.

The outputs from the phonetic encoder 504 are input into the sound edit distance algorithm 506. A sound edit distance as used herein is an edit distance (e.g., a Levenshtein distance) between the phoneme sequence of a suggested search query candidate term and the original search query term. In other words, the sound edit distance algorithm 506 computes an edit distance between a sound code associated with a suggested search query candidate and a sound code associated with the user search query input into the spell corrector model 500. A sound edit distance is determined for each of the suggested search query candidates associated with the user search query. In some examples, when multiple suggested search query candidates are determined for the user search query, the suggested search query that has a sound code with the lowest sound edit distance is output by the spell corrector model 500 as the suggested search query. In these examples, the suggested search query corresponding to a sound code that has the lowest sound edit distance relative to the user search query sound code is selected from the set of the suggested search query candidates. For example, a suggested search query candidate having the least sound edit distance has the highest ranking. In one embodiment, the sound edit distance algorithm 506 corresponds to a Levenshtein distance and the minimum Levenshtein distance is computed between a suggested search query candidate sound code and the user search query sound code to return the corresponding suggested search query as an output from the spell corrector model 500.

FIG. 6 illustrates a block diagram of an example model selection framework 600, according to some embodiments of the present disclosure. The model selection framework 600 is applied for the ensemble spell corrector model 207 and includes using the model selector 209 to select a suggested search query from a plurality of suggested search queries each determined by a spell corrector model from the ensemble spell corrector model 207.

The ensemble spell corrector model 207 shown in FIG. 6 includes a total of seven spell corrector models. The ensemble spell corrector model 207 includes model 1, model 2, model 3, model 4, model 5, model 6, and model 7. Although seven models are shown in FIG. 6, a plurality of spell corrector models according to the present disclosure, such as the ensemble spell corrector model 207, may include fewer or more spell corrector models. Each of the models from the ensemble spell corrector model 207 uses a different dictionary to determine a suggested search query. The suggested search query provides an alternative (e.g., correct) spelling for the original search query that is input by a user and not found in the correctly spelled words corpus 140.

As shown in FIG. 6, model 1 uses dictionary 1, model 2 uses dictionary 2, model 3 uses dictionary 3, model 4 uses dictionary 4, model 5 uses dictionary 5, model 6 uses dictionary 6, and model 7 uses dictionary 7. In an example herein, one or more dictionaries shown in FIG. 6 may correspond to a model dictionary from the model dictionaries 180 shown in FIG. 1. In some examples, model 1, model 3, and model 6 may each be an edit distance model. Model 1, model 3, and model 6 may use a Levenshtein distance algorithm to find permutations within an edit distance of a predefined threshold from the original search query term and compare the permutations (e.g., insertions, deletions, replacements, and transpositions) to the terms in the associated dictionary to determine a suggested search query. The predefined threshold for the edit distance used with model 1, model 3, and model 6 is a value (e.g., Levenshtein distance) of 1, 2, or 3. For example, model 1, model 3, and model 6 are based on a known edit distance model using python, such as Peter Norvig's spell corrector.

While the same type of spell corrector (e.g., edit distance) model may be used for model 1, model 3, and model 6, each of these models may use a different dictionary. Dictionary 1 which is used with model 1 may be a user session based dictionary. A user session based dictionary is based on the search history (e.g., prior search session(s)) of the user who input the user search query. In other words, the user session based dictionary is unique to a particular user. As such, dictionary 1 changes based on the user. Dictionary 1 may be based on the user search history 150 and may include all correctly spelled search queries and their corresponding frequencies from previous searches by a single user associated with the user search query input. In certain examples, dictionary 1 does not exist for a user who has no prior search history. For example, dictionary 1 is empty for a new user inputting a search query for the first time. Given the type of dictionary used with model 1, model 1 may also be referred to as a personalized model. Dictionary 3 which is used with model 3 may be based on a collection of correctly spelled words that have been queried online. For example, dictionary 3 includes a collection of correctly spelled search results, which are tokenized. In particular, dictionary 3 includes medical related queries. Unlike dictionary 1, dictionary 3 may be used for different users. Dictionary 6 which is used with model 6 may be sourced from a database such as OpenSubtitles.

Model 2 may correspond to the model discussed with respect to FIG. 4. As previously discussed, model 2 may be a trained machine learning model. For example, model 2 is a two layer feed-forward network. The input is generated from a concatenation of transformer-based language model embeddings based on the user search query and claims embeddings based on EMR data for the user. In order to generate the embeddings based on the user search query, a transformer-based language model is used. The transformer-based language model is a pre-trained BERT model. Dictionary 2 may include claims embedding data of the user who input the user search query. Like dictionary 1, dictionary 2 may be unique to a particular user. Dictionary 2 may also change based on the user. Model 2 may thus generate personalized results for the suggested search query. Model 4 may be a transformer-based language model. For example, model 4 may be a BERT model. Model 4 may be a pre-trained BERT model. Model 4 may be based on a spell corrector model known as BERTChecker. Dictionary 4 which may be used with model 4 may be based on the one billion words benchmark. In some examples, model 4 generates the embeddings based on the user search query in model 2.

Model 5 may correspond to the model discussed with respect to FIG. 5. As previously discussed, model 5 may include a phonetic encoder which encodes suggested search queries generated for the user search query based on medical occupations tokens and computes a sound edit distance to return the suggested search query that has a sound code with the minimum edit distance relative to the sound code of the user search query. As such, dictionary 5 may include medical occupations tokens.

Model 7 may also be an edit distance model. However, model 7 may differ from model 1, model 3 and model 6. Model 7 may be faster than the other edit distance based models. For example, model 7 is based on a symmetric delete spelling correction algorithm that reduces the complexity of edit candidate generation and dictionary for a given Levenshtein distance. Model 7 may be based on a spell corrector model known as Symspell. Dictionary 7 may be based on two data sources combined by intersection. For example, dictionary 7 includes Google Books Ngram data which provides representative word frequencies and Spell Checker Oriented Word Lists (SCOWL) which ensures genuine English vocabulary.

Upon determining a suggested search query by using an associated dictionary, each of the 7 models from the ensemble spell corrector model 207 outputs a suggested search query based on the associated dictionary. Each of the suggested search queries output by each of the models from the ensemble spell corrector 207 will have a particular spelling. For example, each model from the ensemble spell corrector model 207 either changes the spelling of the user search query, such that the suggested search query has a different spelling, or returns the user search query, such that the suggested search query has the same spelling as the original user search query. The model selector 209 receives a suggested search query output from each spell corrector model of the ensemble spell corrector model 207 and selects one of the suggested search queries. The suggested search query that is selected by the model selector 209 may be the optimal (e.g., best) suggestion for replacing the original search query. For example, the model selector 209 determines which suggested search query among the plurality of the suggested search queries generated has the correct spelling.

The model selector 209 compares each suggested search query determined for each model from the ensemble spell corrector model 207 to the global search history 160 to determine how frequently each suggested search query appears in the global search history 160. The model selector 209 then selects the suggested search query with the highest frequency of occurrence. However, if none of the suggested search queries exists in the global search history 160, then the model selector 209 selects a suggested search query based on a weightage of the associated model in the ensemble spell corrector model 207. In some examples, the weightage is based on the order of the models shown in FIG. 6. For example, model 4 will have a higher weight than models 5-7. While the weightage of the spell corrector models may correspond to the order shown in FIG. 6, other methods for ranking or weighting the models may be possible.

In one particular example, a user enters the following search query "maik a appointmnt", which is misspelled. Each of the spell corrector models 1-7 generates an output of a suggested search query based on their respective dictionaries. However, in some cases, one or models from the ensemble spell corrector model 207 may not output a suggested search query with a correct spelling. In this example, model 4 corrects the search query to "make an appointment" and model 5 updates the search query to "make a appointment". The other models return a suggested search query that is the same as the original user search query. The model selector 209 compares all of the suggested search query outputs, including those that return the same input, with the global search history 160. The model selector 209 then determines that the string "make an appointment" occurred more frequently in the global search history 160 than "make a appointment" and thus selects the "make an appointment" suggested search query.

In cases where neither of the suggested search queries are found in the global search history 160, the model selector 209 prioritizes the selection based on the weightage of the models in the ensemble spell corrector model 207. For example, the model selector 209 looks to the order of the models. In this example, the model selector 209 first looks to the output of model 1, which is the first model in the plurality of models. However, since the output of model 1 is the same as the user search query ("maik a appointmnt"), the model selector 209 evaluates the remaining outputs based on the order of the models until there is a change in a spelling. In this example, the model selector 209 determines that the first change in spelling with respect to the user search query occurs with model 4. Thus, the model selector 209 stops at model 4 and selects "make an appointment" as the output for displaying to the user.

The ensemble spell corrector model 207 of the present disclosure is especially beneficial in determining a correct spelling for a user search query that is the most relevant to a particular user. As discussed above, a user may enter the following misspelled search query "acetahoxamide". The recommended spelling corrections for this query are "acetazolamide" and "acetohexamide". For example, each of the models in the ensemble spell corrector model 207 produces one of these queries as a suggested search query. The model selector 209 looks to model 1 first, and selects "acetazolamide" when this is the output of model 1, demonstrating that the user had previously searched for "acetazolamide" and the term appears in dictionary 1. However, if the user has no prior search history associated with either term, but does have an EMR indicating glaucoma, the model selector 209 selects "acetazolamide" generated by model 2. For example, model 2 uses claims embeddings based on EMR data for the user to determine a suggested search query. In some examples, the model selector 209 looks to the first two models (e.g., model 1 and model 2) of the ensemble spell corrector model 207 in selecting the suggested search query first, since these models generate outputs based on personal user data.

In other examples, the model selector 209 selects a suggested search query from a plurality of suggested search queries based on the frequency of the suggested search query in the global search history 160, when there is no personal historical data associated with the user. For example, the user is a new user using search engine 195 for the first time. In addition, the user has no associated EMR data. In these cases, the model selector 209 would only consider the outputs from models 3-7 and not models 1 and 2. In the example discussed above where the suggested search queries are "acetazolamide" and "acetohexamide", when the user has no historical data, the model selector 209 will select "acetohexamide", since it has been searched more frequently as evidenced by the global search history 160.

In addition to generating suggested search queries that provide for spell correction, the ensemble spell corrector model 207 determines that a user search query is correctly spelled, even when it is not found in the correctly spelled words corpus 140. For example, if all of the models in the ensemble spell corrector 207 each output the search query input, then original search query is determined to be correctly spelled and stored in the correctly spelled words corpus 140 as a new addition.

In general, any process or operation discussed in this disclosure that is understood to be computer-implementable, such as the process illustrated in FIG. 3 as well as the spell correction models and model selector shown in FIGS. 4-5 and 6, respectively, may be performed by one or more processors of a computer system as described herein. A process or process step performed by one or more processors may also be referred to as an operation. The one or more processors may be configured to perform such processes by having access to instructions (e.g., software or computer-readable code) that, when executed by the one or more processors, cause the one or more processors to perform the processes. The instructions may be stored in a memory of the computer system. A processor may be a central processing unit (CPU), a graphics processing unit (GPU), or any suitable types of processing unit.

A computer system, such as a system or device implementing a process or operation in the examples above, may include one or more computing devices. One or more processors of a computer system may be included in a single computing device or distributed among a plurality of computing devices. One or more processors of a computer system may be connected to a data storage device. A memory of the computer system may include the respective memory of each computing device of the plurality of computing devices.

In various embodiments, one or more portions of process 300 may be implemented in, for instance, a chip set including a processor and a memory as shown in FIG. 7. FIG. 7 illustrates an implementation of a computer system that may execute techniques presented herein. The computer system 700 can include a set of instructions that can be executed to cause the computer system 700 to perform any one or more of the methods, system, or computer based functions disclosed herein. The computer system 700 may operate as a standalone device or may be connected, e.g., using a network, to other computer systems or peripheral devices.

Unless specifically stated otherwise, as apparent from the following discussions, it is appreciated that throughout the specification, discussions utilizing terms such as "processing," "computing," "calculating," "determining", "analyzing" or the like, refer to the action and/or processes of a computer or computing system, or similar electronic computing device, that manipulate and/or transform data represented as physical, such as electronic, quantities into other data similarly represented as physical quantities.

In a similar manner, the term "processor" may refer to any device or portion of a device that processes electronic data, e.g., from registers and/or memory to transform that electronic data into other electronic data that, e.g., may be stored in registers and/or memory. A "computer," a "computing machine," a "computing platform," a "computing device," or a "server" may include one or more processors.

In a networked deployment, the computer system 700 may operate in the capacity of a server or as a client user computer in a server-client user network environment, or as a peer computer system in a peer-to-peer (or distributed) network environment. The computer system 700 can also be implemented as or incorporated into various devices, such as a personal computer (PC), a tablet PC, a personal digital assistant (PDA), a mobile device, a palmtop computer, a laptop computer, a desktop computer, a communications device, a wireless telephone, a land-line telephone, a control system, a camera, a scanner, a facsimile machine, a personal trusted device, a web appliance, a network router, switch or bridge, or any other machine capable of executing a set of instructions (sequential or otherwise) that specify actions to be taken by that machine. In a particular implementation, the computer system 700 can be implemented using electronic devices that provide voice, video, or data communication. Further, while a computer system 700 is illustrated as a single system, the term "system" shall also be taken to include any collection of systems or sub-systems that individually or jointly execute a set, or multiple sets, of instructions to perform one or more computer functions.

As illustrated in FIG. 7, the computer system 700 may include a processor 702, e.g., a central processing unit (CPU), a graphics processing unit (GPU), or both. The processor 702 may be a component in a variety of systems. For example, the processor 702 may be part of a standard personal computer or a workstation. The processor 702 may be one or more general processors, digital signal processors, application specific integrated circuits, field programmable gate arrays, servers, networks, digital circuits, analog circuits, combinations thereof, or other now known or later developed devices for analyzing and processing data. The processor 702 may implement a software program, such as code generated manually (i.e., programmed).

The computer system 700 may include a memory 704 that can communicate via a bus 708. The memory 704 may be a main memory, a static memory, or a dynamic memory. The memory 704 may include, but is not limited to computer readable storage media such as various types of volatile and non-volatile storage media, including but not limited to random access memory, read-only memory, programmable read-only memory, electrically programmable read-only memory, electrically erasable read-only memory, flash memory, magnetic tape or disk, optical media and the like. In one implementation, the memory 704 includes a cache or random-access memory for the processor 702. In alternative implementations, the memory 704 is separate from the processor 702, such as a cache memory of a processor, the system memory, or other memory. The memory 704 may be an external storage device or database for storing data. Examples include a hard drive, compact disc ("CD"), digital video disc ("DVD"), memory card, memory stick, floppy disc, universal serial bus ("USB") memory device, or any other device operative to store data. The memory 1004 is operable to store instructions executable by the processor 702. The functions, acts or tasks illustrated in the figures or described herein may be performed by the processor 702 executing the instructions stored in the memory 704. The functions, acts or tasks are independent of the particular type of instructions set, storage media, processor or processing strategy and may be performed by software, hardware, integrated circuits, firm-ware, micro-code and the like, operating alone or in combination. Likewise, processing strategies may include multiprocessing, multitasking, parallel processing and the like.

As shown, the computer system 700 may further include a display 710, such as a liquid crystal display (LCD), an organic light emitting diode (OLED), a flat panel display, a solid-state display, a cathode ray tube (CRT), a projector, a printer or other now known or later developed display device for outputting determined information. The display 710 may act as an interface for the user to see the functioning of the processor 702, or specifically as an interface with the software stored in the memory 704 or in the drive unit 706.

Additionally or alternatively, the computer system 700 may include an input/output device 712 configured to allow a user to interact with any of the components of computer system 700. The input/output device 712 may be a number pad, a keyboard, or a cursor control device, such as a mouse, or a joystick, touch screen display, remote control, or any other device operative to interact with the computer system 700.

The computer system 700 may also or alternatively include drive unit 706 implemented as a disk or optical drive. The drive unit 706 may include a computer-readable medium 722 in which one or more sets of instructions 724, e.g. software, can be embedded. Further, instructions 724 may embody one or more of the methods or logic as described herein. The instructions 724 may reside completely or partially within the memory 704 and/or within the processor 702 during execution by the computer system 700. The memory 704 and the processor 702 also may include computer-readable media as discussed above.

In some systems, a computer-readable medium 722 includes instructions 724 or receives and executes instructions 724 responsive to a propagated signal so that a device connected to a network 190 can communicate voice, video, audio, images, or any other data over the network 190. Further, the instructions 724 may be transmitted or received over the network 190 via a communication port or interface 720, and/or using a bus 708. The communication port or interface 720 may be a part of the processor 702 or may be a separate component. The communication port or interface 720 may be created in software or may be a physical connection in hardware. The communication port or interface 720 may be configured to connect with a network 190, external media, the display 710, or any other components in computer system 700, or combinations thereof. The connection with the network 190 may be a physical connection, such as a wired Ethernet connection or may be established wirelessly as discussed below. Likewise, the additional connections with other components of the computer system 700 may be physical connections or may be established wirelessly. The network 190 may alternatively be directly connected to a bus 1008.

While the computer-readable medium 722 is shown to be a single medium, the term "computer-readable medium" may include a single medium or multiple media, such as a centralized or distributed database, and/or associated caches and servers that store one or more sets of instructions. The term "computer-readable medium" may also include any medium that is capable of storing, encoding, or carrying a set of instructions for execution by a processor or that cause a computer system to perform any one or more of the methods or operations disclosed herein. The computer-readable medium 722 may be non-transitory, and may be tangible.

The computer-readable medium 722 can include a solid-state memory such as a memory card or other package that houses one or more non-volatile read-only memories. The computer-readable medium 722 can be a random-access memory or other volatile re-writable memory. Additionally or alternatively, the computer-readable medium 722 can include a magneto-optical or optical medium, such as a disk or tapes or other storage device to capture carrier wave signals such as a signal communicated over a transmission medium. A digital file attachment to an e-mail or other self-contained information archive or set of archives may be considered a distribution medium that is a tangible storage medium. Accordingly, the disclosure is considered to include any one or more of a computer-readable medium or a distribution medium and other equivalents and successor media, in which data or instructions may be stored.

In an alternative implementation, dedicated hardware implementations, such as application specific integrated circuits, programmable logic arrays and other hardware devices, can be constructed to implement one or more of the methods described herein. Applications that may include the apparatus and systems of various implementations can broadly include a variety of electronic and computer systems. One or more implementations described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

The computer system 700 may be connected to a network 190. The network 190 may define one or more networks including wired or wireless networks. The wireless network may be a cellular telephone network, an 802.11, 802.16, 802.20, or WiMAX network. Further, such networks may include a public network, such as the Internet, a private network, such as an intranet, or combinations thereof, and may utilize a variety of networking protocols now available or later developed including, but not limited to TCP/IP based networking protocols. The network 190 may include wide area networks (WAN), such as the Internet, local area networks (LAN), campus area networks, metropolitan area networks, a direct connection such as through a Universal Serial Bus (USB) port, or any other networks that may allow for data communication. The network 190 may be configured to couple one computing device to another computing device to enable communication of data between the devices. The network 190 may generally be enabled to employ any form of machine-readable media for communicating information from one device to another. The network 190 may include communication methods by which information may travel between computing devices. The network 190 may be divided into sub-networks. The sub-networks may allow access to all of the other components connected thereto or the sub-networks may restrict access between the components. The network 190 may be regarded as a public or private network connection and may include, for example, a virtual private network or an encryption or other security mechanism employed over the public Internet, or the like.

In accordance with various implementations of the present disclosure, the methods described herein may be implemented by software programs executable by a computer system. Further, in an example, non-limited implementation, implementations can include distributed processing, component/object distributed processing, and parallel processing. Alternatively, virtual computer system processing can be constructed to implement one or more of the methods or functionality as described herein.

Although the present specification describes components and functions that may be implemented in particular implementations with reference to particular standards and protocols, the disclosure is not limited to such standards and protocols. For example, standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same or similar functions as those disclosed herein are considered equivalents thereof.

It will be understood that the steps of methods discussed are performed in one embodiment by an appropriate processor (or processors) of a processing (i.e., computer) system executing instructions (computer-readable code) stored in storage. It will also be understood that the disclosure is not limited to any particular implementation or programming technique and that the disclosure may be implemented using any appropriate techniques for implementing the functionality described herein. The disclosure is not limited to any particular programming language or operating system.

It should be appreciated that in the above description of example embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

Thus, while there has been described what are believed to be the preferred embodiments of the invention, those skilled in the art will recognize that other and further modifications may be made thereto without departing from the spirit of the invention, and it is intended to claim all such changes and modifications as falling within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

The above disclosed subject matter is to be considered illustrative, and not restrictive, and the appended claims are intended to cover all such modifications, enhancements, and other implementations, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description. While various implementations of the disclosure have been described, it will be apparent to those of ordinary skill in the art that many more implementations and implementations are possible within the scope of the disclosure. Accordingly, the disclosure is not to be restricted except in light of the attached claims and their equivalents.

The present disclosure furthermore relates to the following aspects.

Example 1. A computer-implemented method for improved spell checking, the method comprising: receiving, by one or more processors, a search query from a user device; determining, by the one or more processors, that the search query does not exist in a data store that stores (a) a corpus of correctly spelled words or (b) forced correction mapping data; in response to the determining: determining, by the one or more processors, a plurality of suggested search queries generated by a plurality of respective spell corrector models, selecting, by the one or more processors, a suggested search query determined using a spell corrector model from the plurality of spell corrector models based on at least one of a frequency of the suggested search query in historical search data or a weightage associated with the spell corrector model, and causing, by the one or more processors, the suggested search query to be displayed on the user device.

Example 2. The computer-implemented method of Example 1, wherein the search query includes one or more terms relating to at least one of a health condition, medical occupation, prescription, or a medical treatment.

Example 3. The computer-implemented method of any of the preceding examples, wherein the data store stores each correctly spelled word from the corpus of correctly spelled words with a corresponding frequency of appearing in a search.

Example 4. The computer-implemented method of Example 3, wherein the search includes one or more searches associated with a user of the user device or a plurality of users.

Example 5. The computer-implemented method of any of the preceding examples, wherein at least two of the spell corrector models from the plurality of the spell corrector models are based on data associated with a user of the user device.

Example 6. The computer-implemented method of Example 5, wherein data associated with the user of the user device includes at least one of: prior search history, one or more prior pharmaceutical claims, one or more previous diagnoses, or one or more previous medical procedures.

Example 7. The computer-implemented method of any of the preceding examples, wherein each spell corrector model from the plurality of spell corrector models uses a different dictionary to determine a suggested search query.

Example 8. The computer-implemented method of any of the preceding examples, wherein the forced correction mapping data is generated based on a prior user session by: receiving a first search query from the user device in a session; receiving a subsequent search query from the user device in the session; determining that the subsequent search query exists in the corpus of correctly spelled words; computing an edit distance between the first search query and the subsequent search query; associating the first search query with the subsequent search query when the edit distance is less than a predefined threshold; and storing the association.

Example 9. The computer-implemented method of any of the preceding examples, further comprising: retrieving electronic medical record (EMR) data associated with a user of the user device; and encoding the EMR data, wherein the EMR data includes at least one of a previous diagnosis, a previous medical procedure, or a previous pharmaceutical claim.

Example 10. The computer-implemented method of Example 9, wherein a first spell corrector model of the plurality of spell corrector models determines a suggested search query by: concatenating the encoded EMR data with an output embedding layer of a transformer-based model; applying the concatenation to a plurality of feed-forward layers of the first spell corrector model to generate a feed-forward output; and applying the feed-forward output as an input to a softmax layer of the first spell corrector model to determine a suggested search query output.

Example 11. The computer-implemented method of any of the preceding examples, wherein a second spell corrector model of the plurality of spell corrector models determines a suggested search query by: determining a list of candidates for the search query input via the user device; generating, using a phonetic encoder, a sound code for the search query and each candidate from the list of candidates; computing a sound edit distance between the sound code of the search query and the sound code for each of the candidates; and selecting a candidate having a minimum sound edit distance for a suggested search query.

Example 12. The computer-implemented method of Example 11, wherein determining a list of candidates is based on a dictionary comprising medical occupations tokens.

Example 13. The computer-implemented method of any of the preceding examples, wherein the plurality of spell corrector models comprises at least five spell corrector models.

Example 14. A system for improved spell checking, the system comprising: a memory having processor-readable instructions stored therein; and one or more processors configured to access the memory and execute the processor-readable instructions to perform operations comprising: receiving a search query from a user device; determining that the search query does not exist in a data store that stores (a) a corpus of correctly spelled words or (b) forced correction mapping data; in response to the determining: determining a plurality of suggested search queries generated by a plurality of respective spell corrector models, selecting a suggested search query determined using a spell corrector model from the plurality of spell corrector models based on at least one of a frequency of the suggested search query in historical search data or a weightage associated with the spell corrector model, and causing the suggested search query to be displayed on the user device.

Example 15. The system of Example 14, wherein at least two of the spell corrector models from the plurality of the spell corrector models are based on data associated with a user of the user device.

Example 16. The system of any of Examples 14-15, wherein a first spell corrector model of the plurality of spell corrector models determines a suggested search query by: concatenating encoded EMR data with an output embedding layer of a transformer-based model; applying the concatenation to a plurality of feed-forward layers of the first spell corrector model to generate a feed-forward output; and applying the feed-forward output as an input to a softmax layer of the first spell corrector model to determine a suggested search query output.

Example 17. The system of any of Examples 14-16, wherein a second spell corrector model of the plurality of spell corrector models determines a suggested search query by: determining a list of candidates for the search query input via the user device; generating, using a phonetic encoder, a sound code for the search query and each candidate from the list of candidates; computing a sound edit distance between the sound code of the search query and the sound code for each of the candidates; and selecting a candidate having a minimum sound edit distance for a suggested search query.

Example 18. A non-transitory computer-readable medium storing a set of instructions for improved spell checking that, when executed by one or more processors, cause the one or more processors to: receive a search query from a user device; determine that the search query does not exist in a data store that stores (a) a corpus of correctly spelled words or (b) forced correction mapping data; in response to the determining: determine a plurality of suggested search queries generated by a plurality of respective spell corrector models, select a suggested search query determined using a spell corrector model from the plurality of spell corrector models based on at least one of a frequency of the suggested search query in historical search data or a weightage associated with the spell corrector model, and cause to display the suggested search query on the user device.

Example 19. The non-transitory computer-readable medium of Example 18, wherein at least two of the spell corrector models from the plurality of the spell corrector models are based on data associated with a user of the user device, the data including at least one of: prior search history, one or more prior pharmaceutical claims, one or more previous diagnoses, or one or more previous medical procedures.

Example 20. The non-transitory computer-readable medium of any of Examples 18-19, wherein at least two of the spell corrector models from the plurality of the spell corrector models are based on data associated with a user of the user device.

What is claimed is:

1. A computer-implemented method for improved spell checking, the method comprising:
receiving, by one or more processors, a search query from a user device;
determining, by the one or more processors, that the search query does not exist in a data store that stores at least one of (a) a corpus of correctly spelled words or (b) forced correction mapping data;
in response to the determining,
selecting, by the one or more processors and among each of a plurality of suggested search queries generated by a respective spell corrector model, one of the plurality of suggested search queries based on at least one of:
a frequency of the suggested search query in historical search data; or
a weightage associated with the spell corrector model that generated the selected suggested search query; and
causing, by the one or more processors, the selected suggested search query to be displayed on the user device.

2. The computer-implemented method of claim 1, wherein the search query includes one or more terms relating to at least one of a health condition, medical occupation, prescription, or a medical treatment.

3. The computer-implemented method of claim 1, wherein the data store stores each correctly spelled word from the corpus of correctly spelled words with a corresponding frequency of appearing in a search.

4. The computer-implemented method of claim 3, wherein the search includes one or more searches associated with a user of the user device or a plurality of users.

5. The computer-implemented method of claim 1, wherein at least two of the spell corrector models from the plurality of the spell corrector models are based on data associated with a user of the user device.

6. The computer-implemented method of claim 5, wherein data associated with the user of the user device includes at least one of: prior search history, one or more prior pharmaceutical claims, one or more previous diagnoses, or one or more previous medical procedures.

7. The computer-implemented method of claim 1, wherein each spell corrector model from the plurality of spell corrector models uses a different dictionary to determine a suggested search query.

8. The computer-implemented method of claim 1, wherein the data store stores the forced correction mapping data, and the forced correction mapping data is generated based on a prior user session by:
receiving a first search query from the user device in a session;
receiving a subsequent search query from the user device in the session;
determining that the subsequent search query exists in the corpus of correctly spelled words;
computing an edit distance between the first search query and the subsequent search query;
associating the first search query with the subsequent search query when the edit distance is less than a predefined threshold; and
storing the association.

9. The computer-implemented method of claim 1, further comprising:
retrieving electronic medical record (EMR) data associated with a user of the user device; and
encoding the EMR data,
wherein the EMR data includes at least one of a previous diagnosis, a previous medical procedure, or a previous pharmaceutical claim.

10. The computer-implemented method of claim 9, wherein a first spell corrector model of the plurality of spell corrector models determines a suggested search query by:
concatenating the encoded EMR data with an output embedding layer of a transformer-based model;
applying the concatenation to a plurality of feed-forward layers of the first spell corrector model to generate a feed-forward output; and
applying the feed-forward output as an input to a softmax layer of the first spell corrector model to determine a suggested search query output.

11. The computer-implemented method of claim 1, wherein a second spell corrector model of the plurality of spell corrector models determines a suggested search query by:
determining a list of candidates for the search query input via the user device;
generating, using a phonetic encoder, a sound code for the search query and each candidate from the list of candidates;
computing a sound edit distance between the sound code of the search query and the sound code for each of the candidates; and
selecting a candidate having a minimum sound edit distance for a suggested search query.

12. The computer-implemented method of claim 11, wherein determining a list of candidates is based on a dictionary comprising medical occupations tokens.

13. The computer-implemented method of claim 1, wherein the plurality of spell corrector models comprises at least five spell corrector models.

14. A system for improved spell checking, the system comprising:
a memory having processor-readable instructions stored therein; and
one or more processors configured to access the memory and execute the processor-readable instructions to perform operations comprising:
receiving a search query from a user device;
determining, by the one or more processors, that the search query does not exist in a data store that stores at least one of (a) a corpus of correctly spelled words or (b) forced correction mapping data;
in response to the determining,
selecting, among each of a plurality of suggested search queries generated by a respective spell corrector model, one of the plurality of suggested search queries based on at least one of:
a frequency of the suggested search query in historical search data; or
a weightage associated with the spell corrector model that generated the selected suggested search query; and
causing the selected suggested search query to be displayed on the user device.

15. The system of claim 14, wherein at least two of the spell corrector models from the plurality of the spell corrector models are based on data associated with a user of the user device.

16. The system of claim 14, wherein a first spell corrector model of the plurality of spell corrector models determines a suggested search query by:
   concatenating encoded EMR data with an output embedding layer of a transformer-based model;
   applying the concatenation to a plurality of feed-forward layers of the first spell corrector model to generate a feed-forward output; and
   applying the feed-forward output as an input to a softmax layer of the first spell corrector model to determine a suggested search query output.

17. The system of claim 14, wherein a second spell corrector model of the plurality of spell corrector models determines a suggested search query by:
   determining a list of candidates for the search query input via the user device;
   generating, using a phonetic encoder, a sound code for the search query and each candidate from the list of candidates;
   computing a sound edit distance between the sound code of the search query and the sound code for each of the candidates; and
   selecting a candidate having a minimum sound edit distance for a suggested search query.

18. A non-transitory computer-readable medium storing a set of instructions for improved spell checking that, when executed by one or more processors, cause the one or more processors to perform operations comprising:
   receiving a search query from a user device;
   determining, by the one or more processors, that the search query does not exist in a data store that stores at least one of (a) a corpus of correctly spelled words or (b) forced correction mapping data;
   in response to the determining,
      selecting, among each of a plurality of suggested search queries generated by a respective spell corrector model, one of the plurality of suggested search queries based on at least one of:
         a frequency of the suggested search query in historical search data; or
         a weightage associated with the spell corrector model that generated the selected suggested search query; and
      causing the selected suggested search query to be displayed on the user device.

19. The non-transitory computer-readable medium of claim 18, wherein at least two of the spell corrector models from the plurality of the spell corrector models are based on data associated with a user of the user device, the data including at least one of: prior search history, one or more prior pharmaceutical claims, one or more previous diagnoses, or one or more previous medical procedures.

20. The non-transitory computer-readable medium of claim 18, wherein at least two of the spell corrector models from the plurality of the spell corrector models are based on data associated with a user of the user device.

* * * * *